(12) United States Patent
Ji

(10) Patent No.: US 12,371,649 B2
(45) Date of Patent: Jul. 29, 2025

(54) BIOLOGICAL SAMPLE IMAGING DEVICE

(71) Applicants: Microlens Technologies Co., Ltd., Beijing, Beijing (CN); Yusi Ji, Beijing (CN)

(72) Inventor: Yusi Ji, Beijing (CN)

(73) Assignees: Microlens Technologies Co., Ltd., Beijing, Beijing (CN); Yusi Ji, Beijing (CN)

( * ) Notice: Subject to any disclaimer, the term of this patent is extended or adjusted under 35 U.S.C. 154(b) by 883 days.

(21) Appl. No.: 17/471,831

(22) Filed: Sep. 10, 2021

(65) Prior Publication Data

US 2022/0154129 A1    May 19, 2022

(30) Foreign Application Priority Data

Nov. 19, 2020  (CN) .......................... 202011308956.X

(51) Int. Cl.
*C12M 1/00* (2006.01)
*C12M 1/34* (2006.01)
(Continued)

(52) U.S. Cl.
CPC ............ *C12M 41/14* (2013.01); *C12M 41/46* (2013.01); *G01N 21/6452* (2013.01); *G01N 21/6486* (2013.01); *G01N 2021/8466* (2013.01)

(58) Field of Classification Search
CPC ... C12M 41/14; C12M 41/46; G01N 21/6452; G01N 21/6486
See application file for complete search history.

(56) References Cited

U.S. PATENT DOCUMENTS

| | | | | |
|---|---|---|---|---|
| 4,250,266 A | * | 2/1981 | Wade .................... | C12M 27/10 435/286.2 |
| 8,709,344 B2 | * | 4/2014 | Bishop .................. | C12M 41/36 366/211 |

(Continued)

FOREIGN PATENT DOCUMENTS

| | | |
|---|---|---|
| CN | 2681624 Y | 3/2005 |
| CN | 203419930 U | 2/2014 |

(Continued)

OTHER PUBLICATIONS

Document entitled CN105990781A Wind-Power Precise Conductive Slip Ring, machine translation of CN 105990781 A provided by ProQuest, original document published 2016. (Year: 2016).*

(Continued)

*Primary Examiner* — Michael A Marcheschi
*Assistant Examiner* — Ashley Lopezlira
(74) *Attorney, Agent, or Firm* — Westman, Champlin & Koehler, P.A.

(57) ABSTRACT

Embodiments of the present disclosure provide a biological sample imaging device, including an incubator with an observation window provided on one side; a biological sample cultivation module provided inside the incubator; an imaging module provided outside the incubator for collecting images of a biological sample cultured in the biological sample cultivation module through the observation window, so that the growth process can be dynamically captured, and the environment in the incubator can be conveniently controlled to adapt to various scientific research scenarios. In addition, the isolation inside and outside the incubator can reduce the interference of the imaging module on the biological sample.

19 Claims, 18 Drawing Sheets

(51) Int. Cl.
  *G01N 21/64* (2006.01)
  *G01N 21/84* (2006.01)

(56) References Cited

U.S. PATENT DOCUMENTS

| | | | | |
|---|---|---|---|---|
| 2003/0031602 | A1* | 2/2003 | Weselak | G01N 35/028 |
| | | | | 435/303.1 |
| 2011/0126565 | A1* | 6/2011 | Tsuruma | C12M 41/14 |
| | | | | 165/59 |
| 2016/0355781 | A1* | 12/2016 | Perez | C12N 13/00 |
| 2018/0346868 | A1* | 12/2018 | Blanchard | C12M 41/46 |
| 2019/0002812 | A1 | 1/2019 | Hagiwara et al. | |
| 2020/0217794 | A1* | 7/2020 | Hagen | G02B 6/08 |
| 2020/0335925 | A1* | 10/2020 | Feng | H01R 39/64 |

FOREIGN PATENT DOCUMENTS

| | | | | | |
|---|---|---|---|---|---|
| CN | 103769251 | A | | 5/2014 | |
| CN | 204174214 | U | | 2/2015 | |
| CN | 105990781 | A | * | 10/2016 | |
| CN | 206452865 | U | | 9/2017 | |
| CN | 206586062 | U | | 10/2017 | |
| CN | 108563252 | A | | 9/2018 | |
| CN | 108795762 | A | | 11/2018 | |
| CN | 208517421 | U | | 2/2019 | |
| CN | 208905343 | U | | 5/2019 | |
| CN | 110455799 | A | * | 11/2019 | ........... G01N 21/453 |
| CN | 210487160 | U | * | 5/2020 | ........... G01L 27/005 |
| CN | 111842467 | A | * | 10/2020 | |

OTHER PUBLICATIONS

Document entitled CN111842467A Movable Spraying Device for Soil Remediation, machine translation of CN 111842467 A provided by ProQuest, original document published 2020. (Year: 2020).*

Document entitled CN210487160U Gas Circuit Assembly and Gas Pressure Calibrator, machine translation of CN 210497160 U provided by ProQuest, original document published 2020. (Year: 2020).*

Document entitled CN110455799A a High-Resolution Holographic Microscope and Method for Living Cell Imaging, machine translation of CN 110455799 A provided by Espacenet, original document published 2019. (Year: 2019).*

Men, Yongfan et al., "A high-throughput imaging system to quantitatively analyze the growth dynamics of plant seedlings", Integrative Biology, Accepted May 9, 2012. (Year: 2012).*

Copy of first Office Action, including Search Report, for Chinese Patent Application No. 202011308956.X, dated May 21, 2021, 27 pages.

Copy of second Office Action, including Search Report, for Chinese Patent Application No. 202011308956.X, dated Aug. 4, 2021, 32 pages.

Men, Yongfan et al., "A high-throughput imaging system to quantitatively analyze the growth dynamics of plant seedlings+†", Integrative Biology, Cite this: Integr. Biol., 2012, 4, 945-952, www.rsc.org/ibiology, Technical Innovation, Accepted May 9, 2012, DOI: 10.1039/c2ib20020a, 8 pages.

Binder, Brad M., "Time-Lapse Imaging to Examine the Growth Kinetics of *Arabidopsis* Seedlings in Response to Ethylene", Chapter 14, Brad M. Binder and G. Eric Schaller (eds.), Ethylene Signaling: Methods and Protocols, Methods in Molecular Biology, vol. 1573, DOI 10.1007/978-1-4939-6854-1_14, © Springer Science+Business Media LLC 2017, 12 pages.

Binder, Brad M., "Rapid Kinetic Analysis of Ethylene Growth Responses in Seedlings: New Insights into Ethylene Signal Transduction", J Plant Growth Regul (2007) 26:131-142, DOI: 10.1007/s00344-007-0004-6, JPGR Journal of Plant Growth Regulation, © Springer Science+Business Media LLC 2017, 12 pages.

* cited by examiner

BIOLOGICAL SAMPLE IMAGING DEVICE

CROSS-REFERENCE TO RELATED APPLICATION(S)

This application claims priority to Chinese Patent Application No. 202011308956.X, filed on Nov. 19, 2020, with the China National Intellectual Property Administration, the content of which is hereby incorporated by reference in its entirety.

TECHNICAL FIELD

The present disclosure relates to the technical field of biological devices, and more particularly, to a biological sample imaging device.

BACKGROUND

In traditional scientific research in botany, due to the experimental method limitations, only the static state of plant phenotypes (i.e., characteristics or parameters describing the growth state of plants) at a certain time section can be studied, reflecting a cumulative effect of all biological dynamic processes before that point in time. However, the plant growth is a combination of a series of time-space-specific processes. Only by observing the dynamic change process can we fully understand the temporal and spatial specificity of plant growth and development regulation.

In the basic scientific research of botany, dynamic temporal and spatial specificity studies and matching experimental techniques are necessary to research fields including but not limited to plant resistance to environmental stress (e.g., high temperature, freeze, salt, anoxia, oxidation damage), light signaling pathway, photosynthesis, plant hormone signaling pathway, plant developmental biology and plant breeding.

Binder (2007) and Binder (2017) describe a method based on CCD image sensors and optical lens, using infrared LED as the imaging lighting source, which can image small plant seedlings (such as *Arabidopsis*) with a length of about 10 mm, and process the acquired images to obtain the growth rate change every 5 minutes. On the basis of the above-mentioned Binder (2007) technology, Men et al. (2012) added an electronically controlled mobile platform controlled by a stepper motor to control the movement of the camera in the horizontal and vertical directions, so that the camera view can be switched between samples. It can shoot and analyze 24 plant seedlings at the same time. All the above devices need to be placed in a dark room to maintain a stable plant growth environment.

The inventor of the present disclosure found that this method cannot conveniently control the growth conditions of plants and cannot adapt to the needs of scientific research scenarios.

SUMMARY

In order to solve the problems in related art, embodiments of the present disclosure provide a biological sample imaging device, comprising:
  an incubator with an observation window provided on one side;
  a biological sample cultivation module provided inside the incubator;
  an imaging module provided outside the incubator for collecting images of a biological sample cultured in the biological sample cultivation module through the observation window.

According to embodiments of the present disclosure, the device further comprises an optical vibration isolation platform, wherein an opening is provided on bottom of the incubator, and the biological sample cultivation module is fixed to the optical vibration isolation platform through the opening.

According to embodiments of the present disclosure, the device further comprises a housing, which is provided outside the incubator and the imaging module and forms a dark room for shielding light.

According to embodiments of the present disclosure, the device further comprises a computer for controlling operation of the incubator, the biological sample cultivation module and the imaging module, and receiving biological sample images.

According to embodiments of the present disclosure, the incubator comprises a temperature control system and a gas control system, wherein:
  the temperature control system includes at least one temperature sensor, a control circuit, a compressor, a condenser, an evaporator, and a circulating fan, wherein the compressor is arranged outside the box; and
  the gas control system includes a gas source, a gas mixing device and a gas sensor.

According to embodiments of the present disclosure, the biological sample cultivation module comprises:
  a rotating frame comprising a rotating platform and a frame body, wherein the frame body is fixed to the rotating platform, and a plurality of mounting positions for petri dish racks are arranged on the frame body; and
  one or more petri dish racks detachably mounted on the mounting positions and configured for fixing one or more petri dish.

According to embodiments of the present disclosure, the frame body is fixed to the rotating platform, comprising first brackets and second brackets, wherein the first brackets are distributed radially, the second bracket is fixed to an end of the first bracket extending out of the rotating platform, and the mounting position is formed in a space between two adjacent second brackets.

According to embodiments of the present disclosure, at least one mounting fixture is fixed on the second bracket, the mounting position is formed between the mounting fixtures of two adjacent second brackets, and the rotating frame comprises at least two mounting fixtures of different heights.

According to embodiments of the present disclosure, the mounting fixture comprises two mounting holes, which are configured to a plurality of petri dish racks, comprising more than two of a small vertical petri dish rack, a large horizontal petri dish rack, an airtight petri dish rack, and a gravity petri dish rack.

According to embodiments of the present disclosure, the petri dish rack comprises a first lighting component and/or a second lighting component, wherein the first lighting component arranged inside a frame of the petri dish rack, and/or the second lighting component arranged on a top of the petri dish rack.

According to embodiments of the present disclosure, the imaging module is arranged on a three-dimensional displacement control device through an adapter assembly; the adapter assembly has a horizontal platform surface which is provided with a guide rail and a positioning pin hole; the guide rail is configured to provide a sliding path; and the positioning pin hole is configured to position the imaging module.

According to embodiments of the present disclosure, the imaging module comprises any one of a microscopic phenotype detection module, a macroscopic phenotype detection module, a luminescence detection module, and a fluorescence detection module.

According to embodiments of the present disclosure, the device further comprises a front imaging lighting module mounted on an end of the three-dimensional displacement control device close to the incubator and configured to provide a front light source for the biological sample cultivation module through the observation window.

According to embodiments of the present disclosure, the device further comprises a back imaging lighting module mounted inside the incubator and configured to provide a back light source for the biological sample cultivation module.

According to the technical solutions provided by the embodiments of the present disclosure, an observation window is provided on one side of the incubator, a biological sample cultivation module is provided inside the incubator, an imaging module is provided outside the incubator for collecting images of a biological sample cultured in the biological sample cultivation module through the observation window, so that the growth process can be dynamically captured while the environment in the incubator can be conveniently controlled to meet the needs of various scientific research scenarios. The interference of the imaging module on the biological sample can be reduced by isolating the inside of the incubator from the outside.

It should be understood that the above general description and the following detailed description are only exemplary and explanatory, and cannot constitute any limitation to present disclosure.

BRIEF DESCRIPTION OF THE DRAWINGS

With reference to the accompanying drawings, the other features, purposes, and benefits of the present disclosure will become more apparent by a detailed description of the following non-restrictive implementations. In the accompanying drawings.

DETAILED DESCRIPTION

Figure 1:
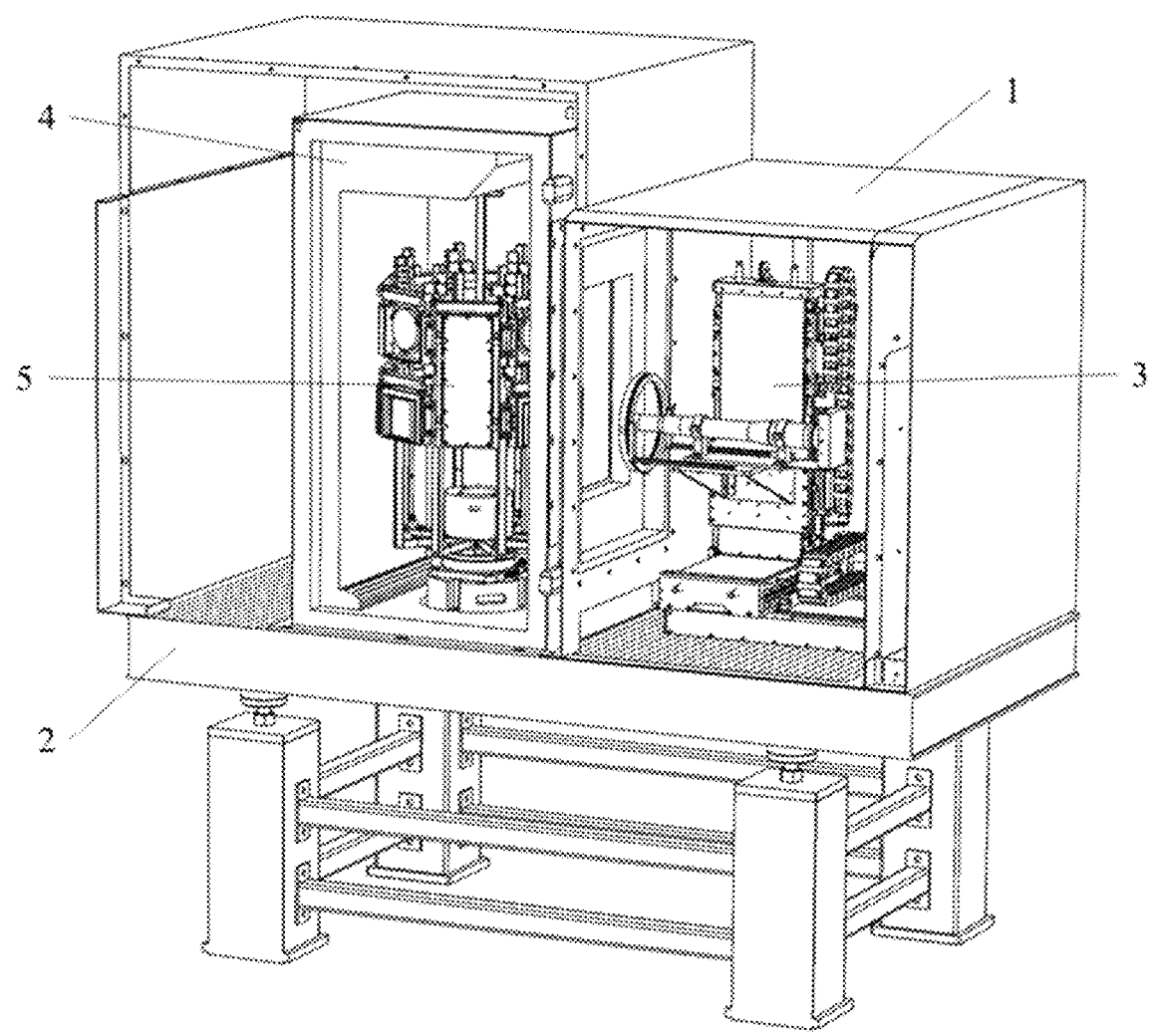
FIG. 1 shows a schematic diagram of a biological sample imaging device according to embodiments of the present disclosure.

Hereinafter, exemplary embodiments of the present disclosure will be described in detail with reference to the accompanying drawings so that those skilled in the art can easily implement them. In addition, for the sake of clarity, parts that are not relevant to describing the exemplary embodiments are omitted in the drawings.

In the present disclosure, it should be understood that terms such as "comprising" or "having" are intended to indicate the existence of the features, numbers, steps, actions, components, parts, or combinations thereof disclosed in this specification, and are not intended to exclude the possibility that one or more other features, numbers, steps, actions, parts, or combinations thereof may exist or be added.

In addition, it should be noted that embodiments and the features in embodiments in the present disclosure can be combined with each other if there is no conflict. Hereinafter, the present disclosure will be described in detail with reference to the attached drawings and embodiments.

Existing technologies such as Binder (2007), Men et al. (2012) and Binder (2017) are unable to conveniently control the growth conditions of plants and cannot adapt to the needs of scientific research scenarios. The biological sample imaging device according to embodiments of the present disclosure provides an incubator with an observation window provided on one side, a biological sample cultivation module provided inside the incubator, an imaging module provided outside the incubator for collecting images of a biological sample cultured in the biological sample cultivation module through the observation window, so that the growth process can be dynamically captured, and the environment in the incubator is conveniently controlled to adapt to various scientific research scenarios. In addition, the interference of the imaging module on the biological sample can be reduced by isolating the inside of the incubator from the outside.

FIG. 1 shows a schematic diagram of a biological sample imaging device according to embodiments of the present disclosure.

As shown in FIG. 1, the biological sample imaging device comprises: an incubator 4 with an observation window provided on one side; a biological sample cultivation module 5 provided inside the incubator 4; an imaging module 3 provided outside the incubator4 for collecting images of a biological sample cultured in the biological sample cultivation module 5 through the observation window.

According to embodiments of the present disclosure, the biological sample may be a plant sample, in particular, a plant seedling sample. The biological sample imaging device provided in embodiments of the present disclosure may be a plant seedling imaging device configured for analyzing the growth state of plant seedlings. A petri dish can be provided inside the biological sample cultivation module 5 for culturing the biological sample. The incubator 4 can flexibly adjust the environmental conditions of the biological sample, including temperature, gas component concentration, etc., to meet the control requirements of various experimental condition variables. The observation window on the side wall of incubator 4 allows the imaging module 3 outside the incubator to collect image data of the biological sample inside the incubator 4 for research.

According to the technical solution provided by embodiments of the present disclosure, the observation window is provided on one side of the incubator, the biological sample cultivation module is provided inside the incubator, the imaging module is provided outside the incubator for collecting the images of a biological sample cultured in the biological sample cultivation module through the observation window, so that the growth process can be dynamically captured, and the environment in the incubator can be conveniently controlled to meet the needs of various scientific research scenarios. Also, the interference of the imaging module on the biological sample can be reduced by isolating the inside of the incubator from the outside thereof.

According to embodiments of the present disclosure, the device further comprises a housing 1, which is provided outside the incubator 4 and the imaging module 5 and forms a dark room for shielding light. When the device is running, it can ensure the dark environment in the imaging darkroom and the incubator 4, which is suitable for detecting the growth status of the biological sample growing in the dark environment, and detecting weak chemiluminescent sample signals through long-term exposure.

According to embodiments of the present disclosure, the device further comprises a computer for controlling operation of the incubator 4, the biological sample cultivation module 5 and the imaging module 3, and receiving biological sample images. The computer can be connected with the control board of each module, and the operation of each module can be controlled by the integrated computer software to obtain, store and analyze the image data of the biological sample.

According to embodiments of the present disclosure, the device also includes an optical vibration isolation platform 2. The imaging module 3, the incubator 4, and the biological sample cultivation module 5, etc. are fixed on the optical vibration isolation platform 2 to isolate vibration and avoid image dithering during imaging. The vibration-generating components such as the compressor and the computer of the incubator 4 are not placed on the optical vibration isolation platform 2.

The following describes the incubator 4 provided by embodiments of the present disclosure.

The incubator has a temperature control function, configured to control the temperature inside the incubator at a predetermined temperature, such as 20° C., 25° C., 37° C., etc., in order to control the temperature variables in the environment to achieve specific purpose. However, the inventor found that in some special scenarios, the requirements for the stability of the objects in the incubator are very high, and the disturbance needs to be reduced as much as possible. The existing technology cannot meet this demand.

In order to solve the above problems, the incubator provided by embodiments of the present disclosure has an opening on the bottom, and the biological sample cultivation module is fixed to the optical vibration isolation platform through the opening, so that the biological sample cultivation module can be fixed through the incubator on the optical vibration isolation platform, and the biological sample cultivation module will not be easily affected by the mechanical strength of the incubator housing and can remain stable. At the same time, the upper surface of the optical vibration isolation platform seals the bottom of the incubator to maintain the airtightness of the incubator.

Figure 2:
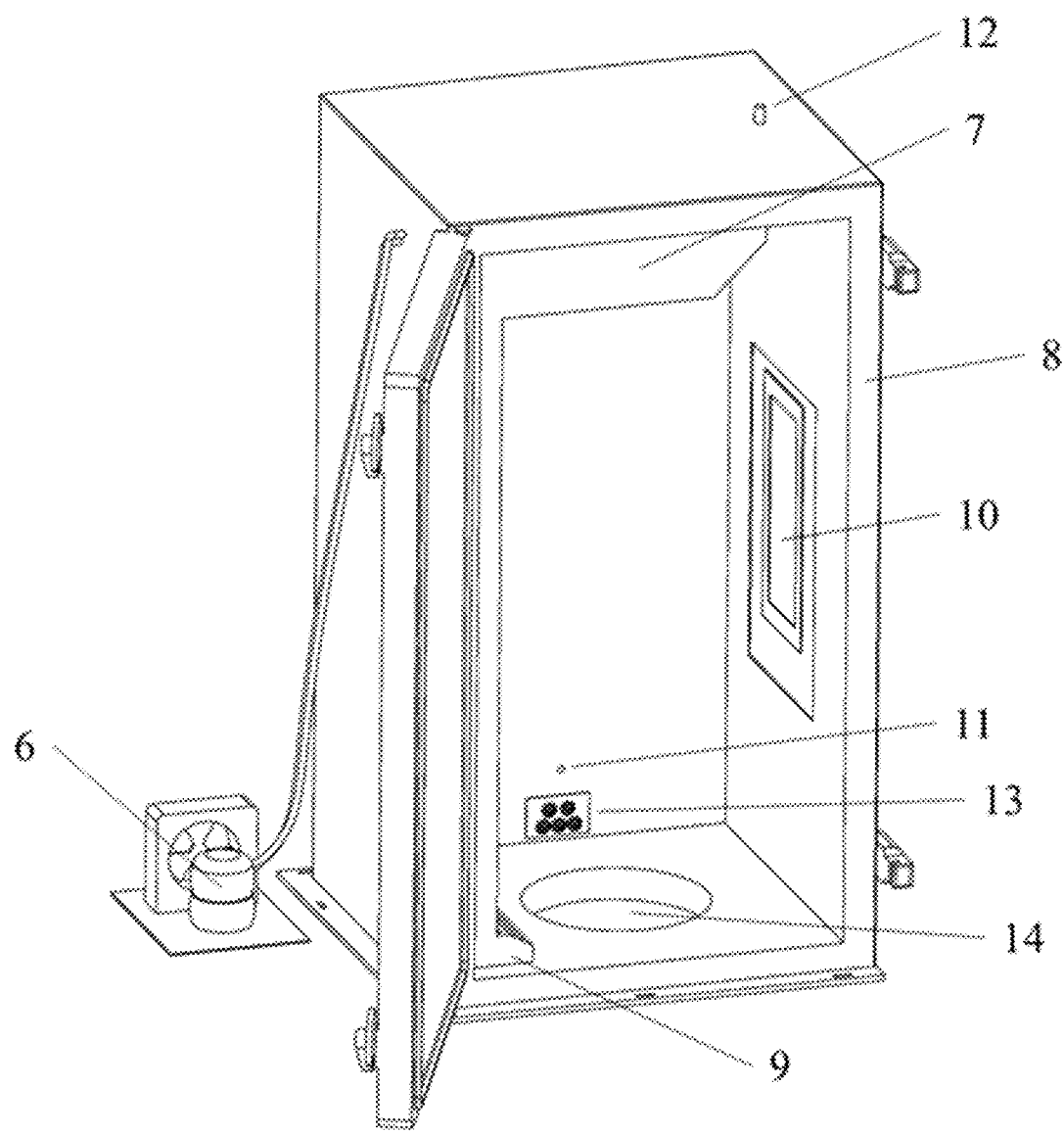
FIG. 2 shows a schematic diagram of an incubator according to embodiments of the present disclosure.

FIG. 2 shows a schematic diagram of an incubator 4 according to embodiments of the present disclosure. As shown in FIG. 2, the incubator 4 includes a box 8 and a temperature control system 7.

The box 8 comprises at least one box door, and the bottom of the box 8 has an opening 14.

The temperature control system 7 includes a temperature sensor, a temperature regulating apparatus, and a control circuit. The control circuit is used to control the operation of the temperature regulating apparatus according to the temperature obtained by the temperature sensor and a target temperature.

According to embodiments of the present disclosure, in order to further enhance the airtightness between the bottom of the incubator 4 and the optical vibration isolation platform 2, a layer of rubber pad is provided at the bottom of the incubator 4. The biological sample cultivation module 5 can be fixed on the optical vibration isolation platform 2 through the opening 14 and the rubber pad.

According to embodiments of the present disclosure, the temperature regulating apparatus includes a compressor 6, a condenser, an evaporator, and a circulating fan, wherein, the compressor 6 is arranged outside the box 8, and the other parts are arranged inside the box 8. For example, as shown in FIG. 2, the compressor 6 is arranged outside the box 8 and is connected to the box 8 by a copper pipe, in order to prevent the vibration generated by the compressor 6 from interfering with the biological sample cultivation module 5 in the box 8 that needs to be kept stable. The box 8 is also provided with a gas outlet 9. When the door of the box 8 is closed, the gas cooled or heated by the temperature regulating apparatus is blown out from the gas outlet 9 and sucked back from the circulating fan to realize the temperature control in the enclosed space of box 8. The gas outlet 9 can be arranged at the bottom of the box, and can be arranged in a long strip shape to increase the cross-sectional area of the outlet, so that the temperature control ability can be improved under the same wind speed.

According to embodiments of the present disclosure, the temperature regulating apparatus can be used to control the inside of the box to maintain a constant temperature, and it can also control the temperature change inside the box according to a predetermined temperature program. For example, the temperature inside the box can be controlled to repeatedly change between 20° C. and 30° C. at a rate of 1° C./minute.

According to embodiments of the present disclosure, both sides of the observation window 10 are covered with coatings to increase light transmittance of the observation window 10 in visible light and/or infrared light waveband.

According to embodiments of the present disclosure, the imaging device 3 outside the box 8 can shoot the objects in the box 8 through the observation window 10. The glass used in the observation window 10 adopts double-sided coating to increase the transmittance of the glass in the visible light and infrared light bands such as 940 nm, in order to reduce the reflection of the infrared lighting source outside the box 8 into the lens, and to reduce the optical signal loss when the object in the box 8 is detected by the sensor outside the box 8.

According to embodiments of the present disclosure, a heating element is mounted around the observation window to prevent the surface of the inner observation window glass from frosting in an internal low-temperature environment.

According to embodiments of the present disclosure, a socket, for example, an aviation socket on an aviation socket panel 13, is provided inside the box 8. The box 8 is also provided with a through hole through which the socket is electrically connected to the outside. The electrical connections between the internal equipment of the box 8 and the outside are all through the aviation socket on the panel to ensure that the wiring is opaque and air-tight.

According to embodiments of the present disclosure, the incubator 4 includes a gas control system, the box 8 is provided with a gas inlet 11 and a gas outlet 12. The gas control system is connected to the gas inlet 11, and delivers gas into the box 8 through the gas inlet 11 and discharges it from the gas outlet 12 to control the concentration of each gas component in the box 8.

According to embodiments of the present disclosure, an exhaust solenoid valve is provided at the gas outlet 12. Under normal conditions, the exhaust solenoid valve is closed to keep the airtightness inside the box. After the gas is ventilated into the box 8, a certain pressure is generated due to the inability to vent, so as to maintain a slight positive gas pressure inside the box, and further avoid the interference of external gas to the internal environment of the box. During the rapid flushing process with high-pressure air, the exhaust solenoid valve can be opened to quickly discharge the gas in the box out of the box.

According to embodiments of the present disclosure, after closing the door of the box, the inside of the box is kept airtight, which can maintain the slight positive gas pressure inside, and the box is opaque except for the observation window. When the exhaust solenoid valve is closed, the gas introduced from the gas inlet 11 generates a slight positive gas pressure inside the box 8, which can prevent external gas from infiltrating into the possible gaps caused by manufacturing process problems and polluting the internal environment.

Figure 3:
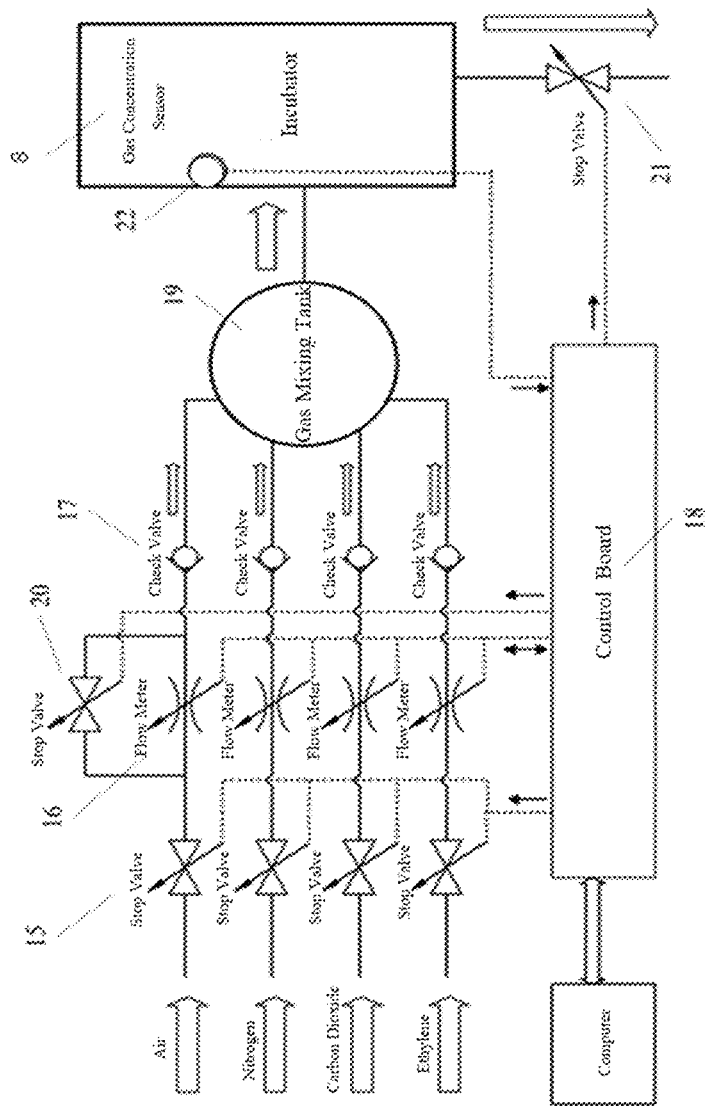
FIG. 3 shows a schematic diagram of a gas control system according to embodiments of the present disclosure.

FIG. 3 shows a schematic diagram of a gas control system according to embodiments of the present disclosure.

As shown in FIG. 3, the gas control system includes a variety of gas sources, a gas mixing device and a gas sensor 22. Wherein, the gas sensor 22 is arranged in the box 8 for detecting the gas concentration in the box 8.

According to embodiments of the present disclosure, the gas mixing device comprises: a plurality of gas paths corresponding to the gas source; a controller, for example, the control board 18 shown in FIG. 3, configured to control gas flow of the plurality of gas paths by controlling stop valves 15 and flow controllers 16 (referred to as flow meter in the figure) of the plurality of gas paths; and a gas mixing tank 19, which is connected to the plurality of gas paths and the gas inlet 11 of the incubator and configured for mixing gas.

According to embodiments of the present disclosure, each gas path includes a stop valve 15, a flow controller 16, and a check valve 17. The controller separately controls the on-off and flow rate of each gas, and mixes the gas in the gas mixing tank 19 and passes it into the box 8 of the incubator. The gas circulation system inside the box 8 can quickly mix the internal gas.

According to embodiments of the present disclosure, the gas source may include, for example, oxygen, carbon dioxide, ethylene and other gas components closely related to plant growth and development. The gas velocity of each path can be controlled by feedback of the detection results of gas sensor 22, so that the concentration of the given gas inside incubator 4 can be maintained stably near the target value. The gas composition and gas concentration range that can be controlled are determined by the type and detection range of the gas sensor, and the various parameters of the control algorithm can be adjusted accordingly, which are not limited to the aforementioned three gases.

Generally, if the target concentration to be controlled is higher than the normal concentration in the atmosphere, it can be achieved by adjusting the mixing ratio and inflow rate of compressed air and high-concentration target gas. If the target concentration is lower than the normal concentration in the atmosphere, the type of gas source can be adjusted. The gas source in embodiments of the present disclosure may also include a nitrogen gas source, which is configured to achieve a scenario where the target concentration is lower than the normal concentration in the atmosphere. For example, for an oxygen-deficient environment, in order to maintain the oxygen concentration at 5%, the mixing ratio and flow rate of compressed air and pure nitrogen can be separately controlled, and the oxygen in the closed incubator can be expelled by nitrogen to achieve low oxygen conditions. For another example, in order to achieve a low carbon dioxide concentration of less than 400 ppm, the mixing ratio and flow rate of the nitrogen-oxygen mixture and pure carbon dioxide can be separately controlled, and the carbon dioxide in the air is expelled by the nitrogen-oxygen mixture to achieve low carbon dioxide conditions.

According to embodiments of the present disclosure, a bypass solenoid valve (also referred to as bypass stop valve) 20 is provided on the gas path corresponding to the air source. When the bypass solenoid valve 20 is opened, high-pressure compressed air can be directly pumped into the box 8 for rapid flushing, and other gas components in the incubator can be quickly drained. At this time, an exhaust solenoid valve (also referred to as gas outlet stop valve) 21 should be opened, so that the gas in the closed incubator is exhausted to the outside of the equipment through an exhaust path.

Next, embodiments of the present disclosure will be described in connection with four typical use scenarios: fresh air, target concentration higher than the atmosphere, target concentration lower than the atmosphere, quick flushing to return to the atmospheric concentration.

1. An embodiment of maintaining a stable gas environment in the incubator without interference from the indoor environment
   a) connect an air compressor or a compressed air cylinder to the air path, and adjust the input air pressure to 0.2~0.4 MPa;
   b) open the stop valve 15 in the air path and the gas outlet stop valve, close the stop valves 15 of the other paths and close the bypass stop valve 20;
   c) enable the air flow controller 16, set the flow to 5-20 L/min.
2. An embodiment of the target concentration to be controlled higher than the normal concentration in the atmosphere: applying 10 ppm ethylene gas treatment to the incubator
   a) connect an air compressor or a compressed air cylinder to the air path, and adjust the input air pressure to 0.2~0.4 MPa; connect an ethylene standard gas cylinder with about 300 times the target concentration to the ethylene path (for example, in case where the target control concentration is 10 ppm, use 3000 ppm concentration of ethylene standard gas with nitrogen or air as carrier gas), and adjust the input pressure to 0.2~0.4 MPa;
   b) open the stop valves 15 in the air path and the ethylene path and the gas outlet stop valve 21, close the stop valves 15 of the other paths, and close the bypass stop valve 20;
   c) enable the flow controllers 16 of the air path and the ethylene path, set the air flow to 5~20 L/min, use PID (Proportion Integral Differential) algorithm to dynamically set the ethylene flow to 0~100 mL/min according to the ethylene sensor reading;
   d) after the ethylene sensor reading reaches the target concentration value, close the gas outlet stop valve 21, set the air flow rate to no more than 1 L/min, and use PID algorithm to dynamically set the air and ethylene flow based on the ethylene sensor reading.
3. An embodiment of the target concentration to be controlled lower than the normal concentration in the atmosphere: applying hypoxia treatment to the incubator (oxygen concentration is 5%)
   a) connect an air compressor or a compressed air cylinder to the air path, connect the nitrogen cylinder to the nitrogen path, and adjust the input air pressure to 0.2~0.4 MPa;
   b) open the stop valves 15 of the nitrogen path and the air path and the gas outlet stop valve 21, close the stop valves 15 of the other paths, and close the bypass stop valve 20;
   c) enable the flow controllers 16 of the nitrogen path and the air path, set the maximum flow rate to 30 L/min, and use PID algorithm to dynamically set the flow rate of nitrogen and air according to the reading of the oxygen sensor;
   d) after the oxygen sensor reading reaches the target concentration value, close the gas outlet stop valve 21, and use PID algorithm to dynamically set the air and nitrogen flow based on the oxygen sensor reading.
4. Quickly return to normal atmospheric level after applying gas treatment (withdraw gas treatment)
   a) connect an air compressor or a compressed air cylinder to the air path, and adjust the input air pressure to 0.2~0.4 MPa;
   b) open the stop valve 15 of the air path, close the stop valves 15 of other paths except the air path, close the flow controller 16 of the air path, and open the bypass stop valve 20 and the gas outlet stop valve 21 to fill the closed incubator with high-pressure air directly and squeeze out the original gas;
   c) after the sensor reading of the corresponding applied gas treatment returning to the threshold line, close the bypass stop valve, enable the air flow controller 16, and set the flow to 5-20 L/min.

Since the existing technology cannot expand the shooting throughput greatly, and the current throughput is far from enough to achieve rigorous statistical analysis, how to increase the shooting throughput to meet the needs of statistical analysis is an urgent problem to be solved.

The biological sample cultivation module provided in the disclosed embodiment can accommodate more biological samples in a limited space through the design of a rotating frame. The biological samples can be respectively aligned with the imaging module through automatic control, thus greatly increasing the sample shooting throughput.

According to embodiments of the present disclosure, the biological sample cultivation module 5 comprises:
   a rotating frame comprising a rotating platform and a frame body, wherein the frame body is fixed to the rotating platform, and a plurality of mounting positions for petri dish racks are arranged on the frame body; and
   one or more petri dish racks detachably mounted on the mounting positions and configured for fixing one or more petri dish.

Figure 4:
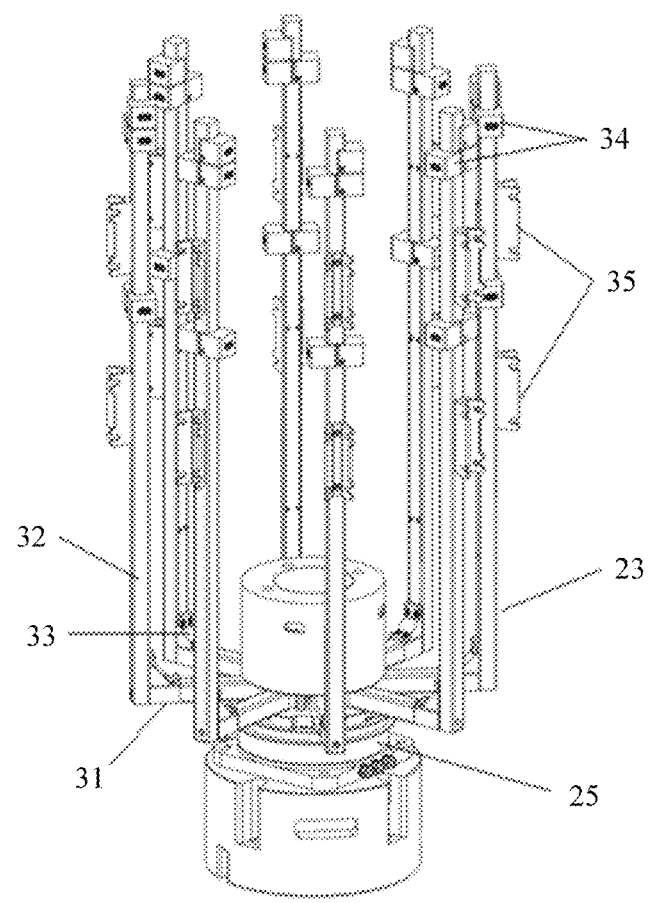
FIG. 4 shows a schematic diagram of a rotating frame according to embodiments of the present disclosure.

FIG. 4 shows a schematic diagram of a rotating frame according to embodiments of the present disclosure;

As shown in FIG. 4, the frame body 23 is fixed to the rotating platform 25. The frame body comprises first brackets 31 and second brackets 32, wherein the first brackets 31 are distributed radially, the second bracket 32 is fixed to an end of the first bracket extending out of the rotating platform 25, and the mounting position is formed in a space between two adjacent second brackets 32 and is configured for fixing the petri dish.

The rotating frame provided by embodiments of the present disclosure can fix a plurality of petri dish racks on the second bracket 32. Under the driving of the rotating platform 25, different dish racks can be respectively aligned with the imaging module 5 set at a fixed position, and thus the imaging analysis of biological samples can be performed on a plurality of petri dish racks, which improves sample analysis throughput.

According to embodiments of the present disclosure, the rotating frame may further include: a corner reinforcement block 33, which is provided at the part where the first bracket 31 and the second bracket 32 are connected, and is used to reinforce the frame body 23 to ensure the stability of the frame body during rotation.

According to embodiments of the present disclosure, a mounting fixture is further provided on the second bracket 32 for fixing the petri dish rack. According to embodiments of the present disclosure, at least one mounting fixture 35 is fixed on the second bracket 32, and the mounting position is formed in a space between the mounting fixtures 35 of two adjacent second brackets 32.

According to embodiments of the present disclosure, an electrical socket interface 34 is provided on the second bracket 32 for electrical connection with the petri dish rack. The electrical socket interface 34 can be fixed on each second bracket 32, and the number of the electrical socket interfaces can also be flexibly set as required. There is no restriction on this in embodiments of the present disclosure.

According to embodiments of the present disclosure, the electrical socket interface 34 includes an electrical circuit connector having control pins for a light source and a servo motor.

In embodiments of the present disclosure, the electrical circuit connector may include a 9-pin flat cable socket, which can simultaneously control 5 light sources and a plurality of servo motors.

The specific pins are defined as follows:
1—light source common cathode/common anode, 2—overhead first light source, 3—overhead second light source, 4—overhead third light source, 5—overhead fourth light source, 6—side light source, 7—servo motor power (VCC pin), 8—servo motor grounding (GND pin), 9—servo motor data bus (DATA pin).

Light sources of different wavelengths and/or light intensities may be arranged in the petri dish rack as the culture light source for biological samples. The electrical socket interface 34 is used to electrically connect with the light source in the petri dish rack, so as to provide a light source condition for culturing the biological sample. For example, the overhead culture light source and the side culture light source can be set on the petri dish rack. Among them, the overhead culture light source is located on the top of the petri dish rack, and the side culture light source is located on the side of the petri dish rack. For the overhead culture light source, a 9-pin plug is used but the cable is only connected to pins 1-5. For the side culture light source, the cable is only connected to pins 1 and 6. The petri dish rack can also be fixed with a gravity module, which can change the direction of gravity of the biological sample in the petri dish. For the gravity module, the cable is only connected to pins 7-9. All modules use 9-pin plugs of the same specification, which can be inserted into any electrical socket interface on the second bracket 32 without distinguishing the location and function of each interface.

The servo motor is controlled by a data bus, and a plurality of motors are connected to the same data bus. According to the address information contained in the data packet, the servo motor with the corresponding address on the bus responds and executes instructions.

The electrical circuit connector can be a flat cable socket, or other types of connectors such as aviation plugs, to achieve rapid connection and disconnection of cables. The number of pins of the connector is not limited to 9 pins. According to the rated current of each pin of the connector, it can be determined whether the multi-channel LED light source adopts common cathode/common anode, or adopts a set of independent cathode/anode pins for each light source. The servo motor can use a single pin as the data pin (TTL signal control mode) or 2 pins as the data pins (RS485 signal control mode) according to the type of data bus. Other pins may also be reserved for subsequent function expansion. There is no restriction on this in embodiments of the present disclosure.

Figure 5A:
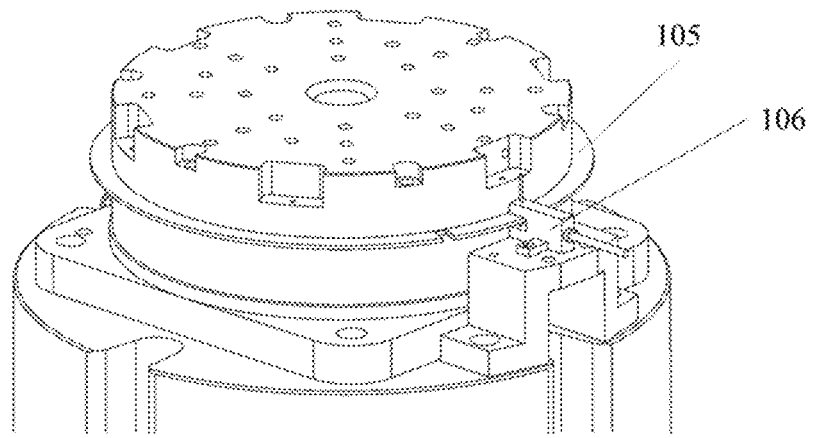
FIG. 5A and FIG. 5B show a schematic diagram of a rotating platform according to embodiments of the present disclosure.
Figure 5B:
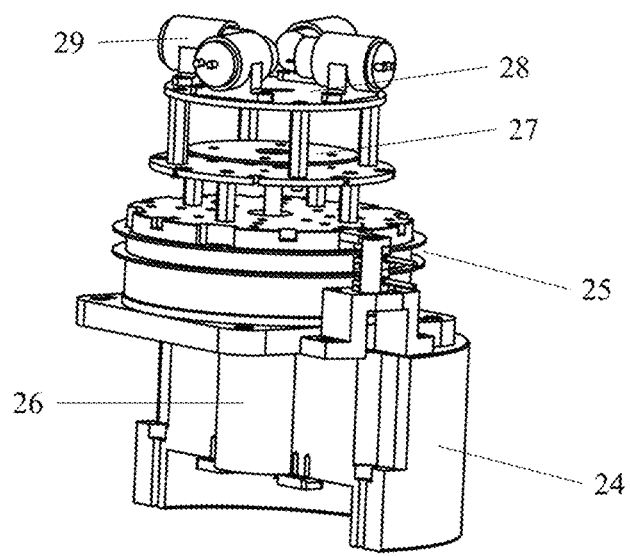

FIG. 5A and FIG. 5B show a schematic diagram of a rotating platform according to embodiments of the present disclosure.

As shown in FIG. 5A, the rotating platform 25 may include: a first base 24; a flange fixed to the first base 24; a baffle 105; and a photoelectric limit switch 106 fixed to the first base 24.

The baffle 105 is fixed at the gap of the flange, and the height of the baffle 105 is configured to the height of the photoelectric limit switch 106. The baffle 105 is provided with a gap through which the optical signal of the photoelectric limit switch 106 can pass.

In embodiments of the present disclosure, the photoelectric limit switch 106 is configured to calibrate a zero point position of the rotating platform 25. When the rotating platform 25 rotates, the optical signal of the photoelectric limit switch 106 is blocked by the baffle 105, and the light signal at the gap can pass, then the zero point position can be calibrated by detecting the light signal, so that the petri dish rack can be aligned with the imaging device.

An exemplary calibration method is as follows:
a) rotate counterclockwise at a speed of about 25°/s until the photoelectric limit switch signal is turned on and stop rotating;
b) rotate clockwise at a speed of about 10°/s until the photoelectric limit switch signal is off and stop rotating;
c) rotate counterclockwise at a speed of about 0.1°/s until the photoelectric limit switch signal is turned on and stop rotating;
d) rotate 1° clockwise at a normal driving speed and set the current position as the zero point.

Precise positioning of the biological sample in the petri dish rack with respect to the imaging device can be realized by calibrating the zero point position using the foregoing method, whereby improving the accuracy of biological sample analysis.

Those of ordinary skill in the art should know that other clockwise and counterclockwise rotation modes and rotation speeds can also be used to calibrate the zero point position, which are not limited to embodiments of the present disclosure.

As shown in FIG. 5B, the rotating frame further includes: a wire distributor plate 27 fixed above the rotating platform 25, wherein, the rotating platform 25 is provided with a conductive slip ring 26, and the cables connected to the electrical socket interface 34 are merged via the wire distributor plate 27 to be electrically connected to the conductive slip ring 26.

In embodiments of the present disclosure, the number of electrical socket interfaces 34 can correspond to the number of petri dish racks, so that the electrical socket interface 34 and can be connected to a nearby petri dish rack. The cables drawn from the different second brackets 32 can be merged via the wiring board 27 and electrically connected to the conductive slip ring 26 inside the rotating platform 25 to ensure that the cable can rotate along with the petri dish rack without cable entanglement, and the electrical signal can be reliably transmitted from the conductive slip ring 26 to the electrical socket interface 34 during the rotating process of the petri dish rack driven by the second brackets 32.

According to embodiments of the present disclosure, a plurality of mounting holes are provided on the top of the rotating platform 25, and the first bracket 31 and the wire distributor plate 27 are fixed through the mounting holes. The first bracket 31 is fixed between the wire distributor plate 27 and the rotating platform 25. The rotating platform 25 is also provided with a central through hole. After being merged via the wire distributor plate 27, the cables connected to the electrical socket interfaces 34 are electrically connected to the conductive slip ring 26 through the central through hole.

According to embodiments of the present disclosure, the mounting holes include: bracket mounting holes and wire distributor plate mounting holes. The bracket mounting holes and the wire distributor plate mounting holes are arranged at intervals. The first brackets 31 are fixed through the bracket mounting holes to form a radial distribution. The wire distributor plate 27 is fixed on the upper side of the rotating platform 25 through the wire distributor plate mounting holes. The first bracket 31 extends from a gap between the vertical mounting fixtures for fixing the wire distributor plate 27 to the outside of the table surface of the rotating platform 25 and forms a free end. The second bracket 32 is mounted on the free end.

According to embodiments of the present disclosure, there are at least two sets of mounting holes for the brackets, so as to form at least one set of adjacent second brackets 32 to facilitate fixing the petri dish rack in the space portion of the adjacent second brackets 32.

According to embodiments of the present disclosure, there are 8 sets of bracket mounting holes, and the angle between adjacent sets is 45°, so as to form an eight-direction main bracket, that is, the number of the second brackets 32 is 8. There are 8 sets of adjacent second brackets 32 for fixing the petri dish racks.

Those of ordinary skill in the art should know that the bracket mounting holes can be in other sets, and the angle between adjacent sets can also be other angles, so as to form a main bracket with other number of directions than eight directions. This disclosure does not limit this.

In embodiments of the present disclosure, each set of bracket mounting holes can be configured to fix one first bracket 31, so there are 8 sets of adjacent second bracket 32 and 8 sets of adjacent first bracket 31. After petri dishes are fixed to the adjacent second brackets 32, the imaging device at a fixed position can be rotated to make the petri dish rack in each direction align with the imaging device in turn, and then perform imaging analysis of the biological sample. It should be noted that a plurality of petri dish racks can be set at different heights on the second brackets 32. When performing imaging analysis, it is only necessary to adjust the height of the imaging device to image the biological sample in the petri dish rack without adjusting the petri dish rack.

In embodiments of the present disclosure, the number of bracket mounting holes in each set can be 1-5 to provide support for the frame body 23. The specific number can be flexibly adjusted according to needs. There is no restriction on this in embodiments of the present disclosure.

According to embodiments of the present disclosure, the conductive slip ring 26 includes a stator part and a rotor part. The rotor part is fixed to the table surface of the rotating platform 25. The stator part is fixed on the first base 24 of the rotating platform 25.

According to embodiments of the present disclosure, the rotating frame further includes: a gas pump fixing plate 28, a plurality of gas pump damping sleeves, and a gas pump 29. The gas pump fixing plate 28 is fixed above the wire distributor plate 27. The plurality of gas pump damping sleeves are fixed on the gas pump fixing plate. The gas pump 29 is arranged inside the gas pump damping sleeves. The gas pump 29 is used for gas exchange between inside and outside of the petri dish rack.

In embodiments of the present disclosure, air, oxygen, carbon dioxide, ethylene and other gases can be pumped into the petri dish rack through the gas pump 29, so that the air composition of the airtight petri dish is consistent with that in the incubator to facilitate research the growth state of plants under the experimental conditions thus to meet the requirements of different experimental conditions.

According to embodiments of the present disclosure, the rotating frame further includes an electrical equipment cover 30 fixed above the first bracket 31. The electrical equipment cover 30 is provided with a gas pump tube outlet, and the gas pump tube connected to the gas pump 29 communicates with the petri dish rack through the gas pump tube outlet.

According to embodiments of the present disclosure, the rotating frame further includes a pneumatic connector connected to the gas pipeline of the gas pump 29 and arranged on the second bracket 32.

In embodiments of the present disclosure, the pneumatic connector can be arranged on the side of the electrical socket interface 34. For example, a connector (quick-plug, quick-screw or pagoda connector) for connecting a pneumatic hose can be mounted and connected to the gas pump 29 through a hose buried in the frame body 23, and connected to the inlet opening of the petri dish rack through the hose.

According to embodiments of the present disclosure, the rotating frame further includes a liquid delivery connector (not shown in the figure), which is connected to the liquid pipeline of the conductive slip ring 26 and is arranged on the second bracket 32.

In embodiments of the present disclosure, the liquid delivery connector may be arranged on the side of the electrical socket interface 34 to provide culture fluid circulation for the biological sample in each petri dish rack. When connecting a liquid pipeline, the conductive slip ring 26 should be configured to an electro-hydraulic hybrid slip ring, and other components of the liquid pipeline such as a culture fluid storage bottle and a peristaltic pump should be connected by a hose and introduced into the frame body 23 through the conductive slip ring 26.

According to the technical solution of embodiments of the present disclosure, more biological samples can be accommodated by the rotating frame to improve the sample analysis throughput.

Referring back to FIG. 4, according to embodiments of the present disclosure, the mounting fixture 35 may include two mounting holes for compatibility with a plurality of types of petri dish racks, including more than two kinds of small vertical petri dish racks, large horizontal petri dish racks, airtight petri dish rack and gravity petri dish rack.

Figure 6:
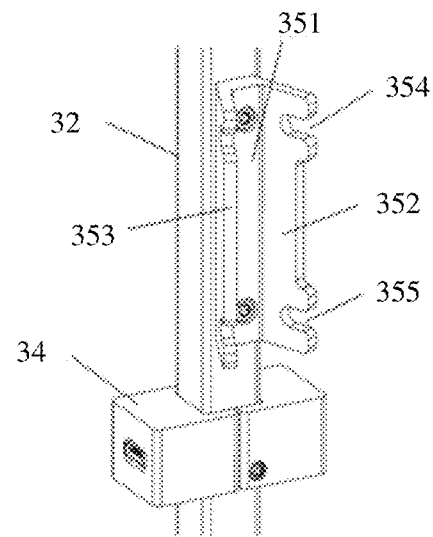
FIG. 6 shows a schematic diagram of a mounting fixture according to embodiments of the present disclosure.

FIG. 6 shows a schematic diagram of a mounting fixture 35 according to embodiments of the present disclosure.

As shown in FIG. 6, the mounting fixture 35 may include: a bracket fixing portion 351; and a first bracket portion 352 and a second bracket portion 353 arranged in pairs. The first bracket portion 352 and the second bracket portion 353 are respectively located on both sides of the bracket fixing part 351. The first bracket portion 352 and the second bracket portion 353 are both provided with at least two mounting holes. The mounting holes form a row of mounting positions.

In embodiments of the present disclosure, the first bracket portion 352 and the second bracket portion 353 are arranged at obtuse angles with respect to the bracket fixing portion 351, thereby presenting an open-close state, which facilitates the operation of fixing the petri dish racks.

In embodiments of the present disclosure, the mounting holes include an upper mounting hole 354 and a lower mounting hole 355. The upper mounting hole 354 and the lower mounting hole 355 constitute a row of mounting positions.

In embodiments of the present disclosure, the upper mounting hole 354 and the lower mounting hole 355 may be through holes or U-shaped grooves. Screws, nuts and other parts can be used to fix the petri dish racks through the through holes or U-shaped grooves. Alternatively, the upper mounting hole 354 and the lower mounting hole 355 may be L-shaped grooves, and screws may be pushed into the lateral part of the L-shaped groove and then slide down into the vertical part to achieve fixation, which makes it easier to determine the front and rear positions.

In embodiments of the present disclosure, a row of mounting positions is not limited to two mounting holes, and a row of mounting positions can also be composed of a plurality of mounting holes. According to the size of the petri dish racks, suitable mounting holes on the mounting positions are selected for fixing. There is no restriction on this in embodiments of the present disclosure.

According to embodiments of the present disclosure, the mounting fixtures 35 are fixed at different heights of the same second bracket 32; and/or the mounting fixtures 35 are fixed at the same height of several second brackets 32.

According to embodiments of the present disclosure, the rotating frame includes at least two mounting fixtures 35 fixed at different heights.

In embodiments of the present disclosure, multiple mounting fixtures 35 can be provided on each second bracket 32, and the height of the mounting fixtures 35 provided on different second brackets 32 are the same, so that the mounting position on the different second bracket 32 are close in height, which facilitates to use the mounting positions to fix a plurality of petri dish racks on the frame body 23 in layers, thus to increase the number of the fixed petri dish racks.

It can be understood that if it is necessary to fix a larger number of petri dish racks, it is only necessary to increase the height of the second bracket 32 and the number of the mounting fixtures 35 accordingly, and set more layers of mounting positions. The details will not be repeated here.

According to embodiments of the present disclosure, the heights of the mounting holes on the two mounting fixtures 35 for fixing the same petri dish rack are matched, and the heights of the two mounting fixtures 35 are the same or different.

In embodiments of the present disclosure, the two mounting fixtures 35 that fix the same petri dish rack may be universal components. When the heights of the two mounting fixtures are the same, the mounting holes on the mounting position are aligned, which is convenient for fixing the petri dish rack.

In embodiments of the present disclosure, when one or more mounting holes of the mounting fixtures 35 of the plurality of second brackets 32 can be misaligned, and other mounting holes can be aligned, then a plurality of petri dish racks can also be fixed in layers by using the mounting positions. There is no restriction on this in embodiments of the present disclosure.

According to embodiments of the present disclosure, a row of mounting positions of the mounting fixture 35 comprises two mounting holes for mounting a small petri dish rack on one side of the mounting fixture 35; or a row of mounting positions of the mounting fixture 35 comprises more than four mounting holes, which are configured to mount two or more small petri dish racks or at least one large petri dish rack on the left or right side of the mounting fixtures 35; or the lengths of the mounting fixtures 35 on the two adjacent second brackets 32 are different, and the height of the mounting holes on the longer mounting fixture 35 should match that of the mounting holes on at least one shorter mounting fixture 35.

In embodiments of the present disclosure, for example, two mounting holes or four mounting holes may be provided as a row of mounting positions on the mounting fixture 35. Fixing a small petri dish rack usually requires two mounting holes to ensure stability. Therefore, mounting fixtures 35 of two mounting holes can be used to fix a small petri dish rack, or mounting fixtures of four mounting holes can be used to fix two small petri dish racks. Of course, it is also possible to fix a large petri dish rack with the mounting fixtures 35 of four mounting holes to ensure stability. Similarly, petri dish racks of different sizes and numbers can be mounted according to the number of mounting holes opened on the mounting fixtures 35. There is no restriction on this in embodiments of the present disclosure.

In embodiments of the present disclosure, the mounting fixture 35 may be a non-universal component, that is, the length of the mounting fixture 35 of two adjacent second brackets 32 may be different. When fixing the petri dish rack, the height of the mounting holes of the longer mount position fixture 35 should match that of the mounting holes on at least one shorter mounting fixture 35, for example, after the mounting holes are aligned or one or several mounting holes are misaligned and the other mounting holes are aligned, a petri dish rack can be fixed.

Figure 7:
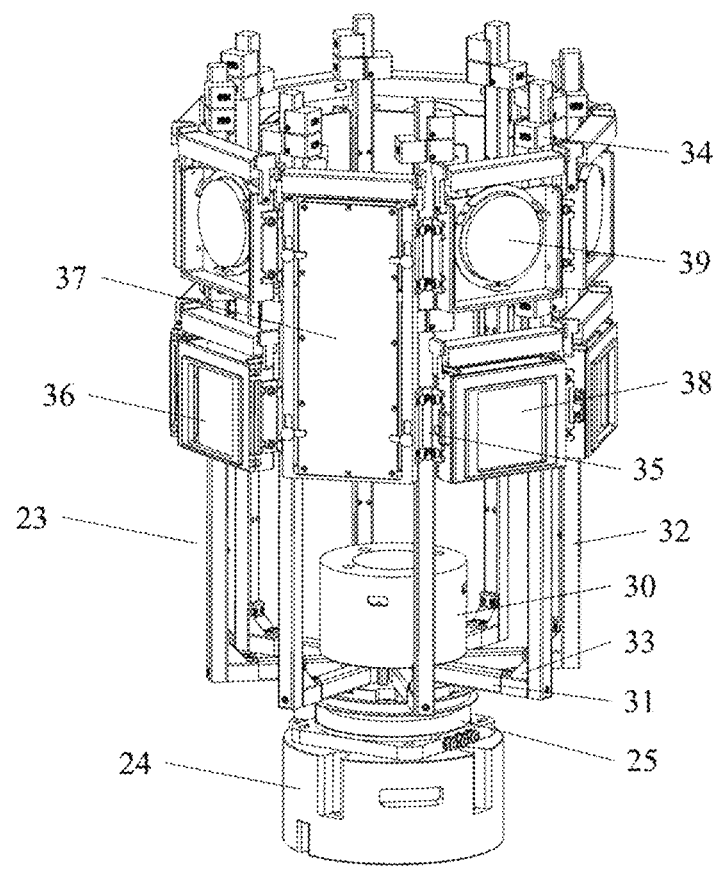
FIG. 7 shows a schematic diagram of a rotating frame with a plurality of petri dish racks mounted thereon according to embodiments of the present disclosure.

FIG. 7 shows a schematic diagram of a rotating frame arranged with a plurality of petri dish racks according to embodiments of the present disclosure.

As shown in FIG. 7, a small vertical petri dish rack 36, a large horizontal petri dish rack 37, an airtight petri dish rack 38 and a gravity petri dish rack 39 are mounted on the rotating frame. Among them, the small vertical petri dish rack 36, the airtight petri dish rack 38, and the gravity petri dish rack 39 occupy one mounting position on the rotating frame, and the large horizontal petri dish rack 37 occupies two mounting positions on the rotating frame.

The rotating frame provided by embodiments of the present disclosure can accommodate the culture devices with different sizes according to different types of samples and required culture methods through the layer arrangement of the mounting fixtures, to adapt to different sizes of petri dishes and samples; and can fix the culture device in the frame in a horizontal, vertical or other form according to the growth habit of the sample to facilitate cultivation and observation, and can accommodate more biological samples, thus to improve the throughput of sample analysis.

The various petri dish racks of embodiments of the present disclosure are introduced below.

According to embodiments of the present disclosure, a small vertical petri dish rack or a large horizontal petri dish rack includes:

a frame with at least two mounting holes provided on both sides of the frame;

a back cover fixedly connected to one side of the frame to form a groove-shaped space; and a fixing component arranged on the side of the frame away from the back cover and configured for fixing the petri dish in the groove-shaped space.

The technical solution provided by embodiments of the present disclosure utilizes the frame and the fixing components to quickly fix the sample on the observation device or quickly replace the sample.

According to embodiments of the present disclosure, the frame has a rectangular shape or a rectangular shape with an opening on one side, and its interior is hollow. The back cover is fixed on one side of the frame, and is made of a transparent material for observing and shooting the internal situation of the small vertical petri dish rack or the large horizontal petri dish rack. The small vertical petri dish rack or the large horizontal petri dish rack can accommodate rectangular or circular plastic petri dishes, and the petri dishes can be placed in the frame vertically. The petri dish is sterilized with ethylene oxide or cobalt-60 radiation before use, and contains a high-temperature sterilized medium which contains biological samples, such as plant seedling samples. The fixing component is arranged on one side of the frame away from the back cover, and can be any one of a steel bar with screws, a spring clip, a spring plate, etc., to stably fix the petri dish in the frame, or hold the petri dish against the back cover to prevent the petri dish from displacement during use.

Figure 8:
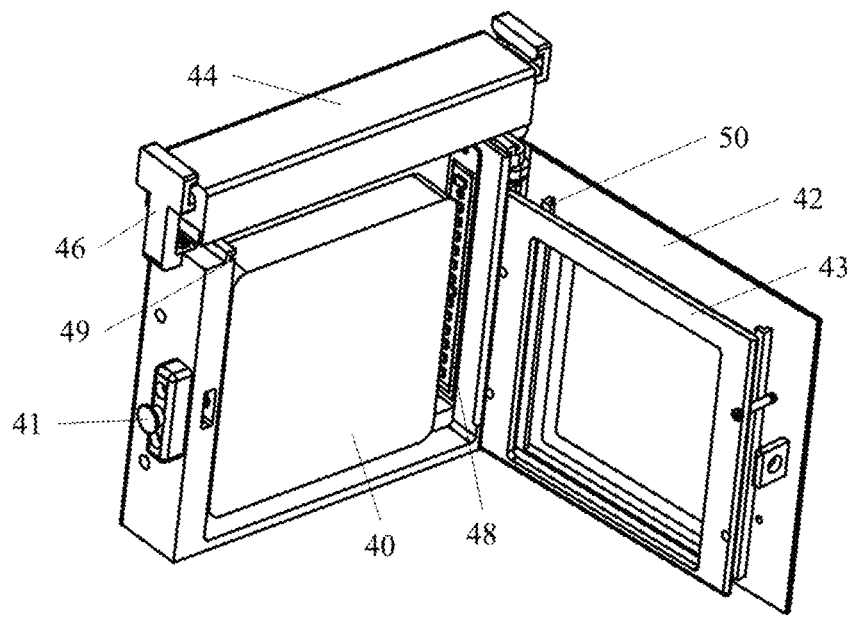
FIG. 8 shows a schematic diagram of a small vertical petri dish rack according to embodiments of the present disclosure.

FIG. 8 shows a schematic diagram of a small vertical petri dish rack according to embodiments of the present disclosure.

As shown in FIG. 8, the fixing component may include a first front cover 42, a door pin 41, a spring sheet 43, a rotating shaft, and a lock catch. The rotating shaft is mounted on one side of the frame away from the back cover. The first front cover 42 is fixedly connected to the rotating shaft, and can rotate relative to the frame with the rotating shaft as an axis. The spring sheet 43 is arranged on the inner side of the first front cover 42. The door pin 41 is provided in the frame. The lock catch is provided at a position corresponding to the door pin inside the first front cover, and the first front cover 42 is locked with the frame by the door pin 41 and the lock catch in the closed state. When the petri dish 40 is placed, the door pin 41 and the first front cover 42 are opened first, and after the petri dish 40 is placed, the first front cover 42 is closed and it is locked by the door pin 41. In the closed state, the spring sheet 43 is placed between the petri dish 40 and the first front cover 42, and the spring sheet 43 stably fixes the petri dish 40 in the frame by elastic force, or puts the petri dish 40 against the back cover to prevent displacement during use.

According to embodiments of the present disclosure, the petri dish 40 may be a disposable plastic transparent petri dish, for example, it may be a 10*10 cm square non-compartment petri dish. The culture medium can be set in the petri dish 40. The configuration method of the culture medium includes: pouring, in a clean bench, the culture medium cooled to about 60° C. into the bottom of the petri dish placed horizontally with a thickness of about 3~4 mm, and covering the lid of the petri dish and waiting for it to solidify for later use. The culture device can be used to cultivate plant samples. The sterilized seeds can be placed on the surface of the medium using tweezers, the petri dish can be sealed with a sealing film, and then is placed in the culture device and fixed by the fixing component, and then placed vertically or horizontally on the fixing bracket. When the culture device is placed vertically, the plant will grow up close to the surface of the medium from the beginning of germination. Alternatively, the normally growing plant sample can be placed gently with tweezers on the medium to ensure that all parts of the plant are close to the surface of the medium. Researchers can observe the growth of plants from one side of the culture medium to prevent water droplets from condensing on the petri dish cover and obstructing the line of sight.

Figure 10:
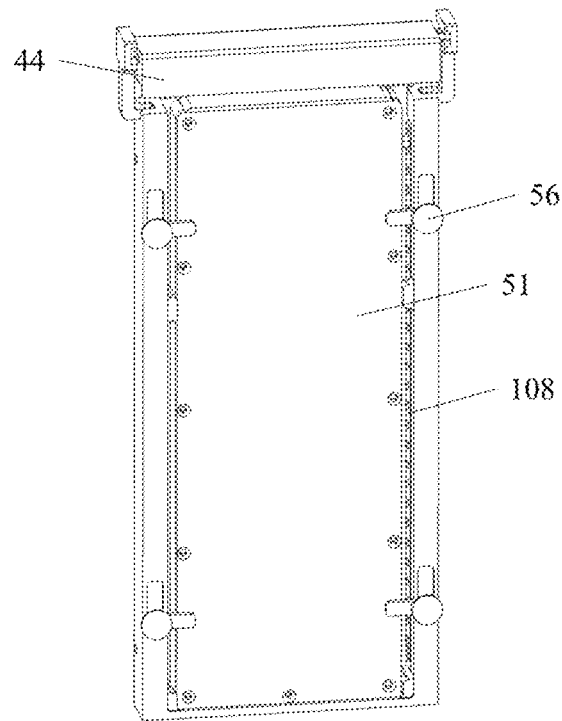
FIG. 10 shows a schematic diagram of a large horizontal petri dish rack according to embodiments of the present disclosure.

FIG. 10 shows a schematic diagram of a large horizontal petri dish rack 37 according to embodiments of the present disclosure.

As shown in FIG. 10, the fixing component may be at least two spring clamps 56, each of which includes a rotating shaft, a spring and a clamping jaw. The rotating shaft is arranged at the center of the spring and can move along the direction of the rotating shaft. The clamping jaw is fixedly connected to the rotating shaft and the spring, and the spring drives the clamping jaw to provide pressure to the frame. The clamping jaw can rotate relative to the frame using the rotating shaft as an axis. The spring clamps 56 are respectively arranged on one side of the frame away from the back cover. Before putting into the petri dish 51, the spring clamps 56 are rotated to make the clamping jaws parallel to the frame. After putting into the petri dish 51, the spring clamps 56 are pulled out and rotated so that the clamping jaws face the direction of the petri dish 51. The spring clamps 56 stably fix the petri dish 51 in the frame, or press the petri dish 51 against the back cover to prevent displacement during use. The petri dish 51 may be a rectangular petri dish.

Figure 11:
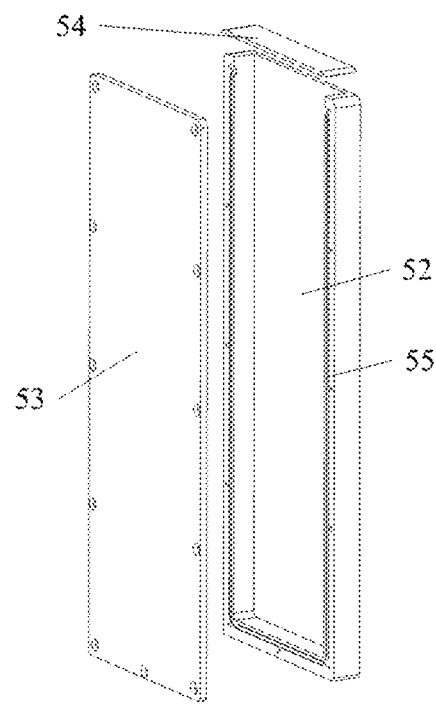
FIG. 11 shows a schematic diagram of a rectangular petri dish rack according to embodiments of the present disclosure.

According to embodiments of the present disclosure, as shown in FIG. 11, the petri dish 40 includes a front plate 53, a rear plate 52, and a top plate 54. A sealing component 55 is provided between the front plate 53 and the rear plate 52 and is detachably connected. The top plate 54 is detachably arranged on one side of the front plate 53 and the rear plate 52, and forms a closed petri dish 51 with the front plate 53 and the rear plate 52. The front plate 53 and the rear plate can be fixed by screws, buckles or other detachable ways. The sealing component 55 may include a rubber sealing ring or a sealing rubber strip, etc., to ensure the air tightness of the petri dish 51. The top plate 54 can cover the top opening of the petri dish 51 to prevent the internal culture medium from being contaminated by external microorganisms. In order to ensure the respiration of the plants in the petri dish 51 during the use of the petri dish 51, an elastic sealing film can be used instead of the top plate 54 to seal the top opening of the petri dish 51, so as to achieve the requirements of ventilation, waterproofing, and prevention of pollution for plant culture. The detachable design is convenient for repeated use, and it is convenient to disassemble, wash and sterilize after use, and reconfigure the medium for plant cultivation. The petri dish 40 can be made of transparent acrylic material and can be used repeatedly. Before preparing the plant sample for cultivation, it needs to be sterilized by methods such as ethylene oxide, and the high-temperature sterilized plant culture medium is poured into the petri dish. Plant seeds are placed on the horizontal surface of the culture medium. After germination, the roots grow into the permeable medium, and the stems are exposed to the air in the petri dish.

In the process of plant sample cultivation, there is a need to change the direction of light to study the phototropic response of plants. However, the prior art equipment cannot guarantee that every plant in a large-scale experiment can be subjected to the illumination of the same distance, angle and intensity. For light is a very important factor in the process of plant growth, the intensity, angle, and wavelength of the light can all directly affect plant growth.

According to embodiments of the present disclosure, the petri dish rack may further include at least one first lighting component arranged inside the frame, for example, the first side light source 48 shown in FIG. 8 and the second side light source 108 shown in FIG. 10. The first lighting component can be fixed on the inner side of the frame by screws or buckles. The first lighting component may be an LED light source for cultivation. In this device, the first lighting component is mounted in a specific position, and can set the same lighting distance and angle, which is convenient for controlling the lighting variable.

According to embodiments of the present disclosure, the petri dish rack may include a second lighting component arranged on the top, for example, the overhead light source 44 as shown in FIG. 8 and FIG. 10.

Figure 9:
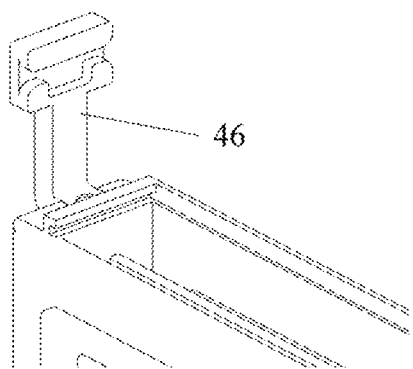
FIG. 9 shows a schematic diagram of a fixing claw according to embodiments of the present disclosure.

According to embodiments of the present disclosure, as shown in FIG. 8, FIG. 9 and FIG. 10, the petri dish rack may further include at least two fixing claws 46 which are arranged oppositely on the top of the frame. The upper part of the fixing claw 46 is provided with a clamping groove, and both ends of the second lighting component are pushed into the clamping grooves and fixed on the fixing claws 46. The fixing claws 46 are fixed at two right angles on one side of the frame, and are each provided with a clamping groove on the adjacent side. The clamping grooves of the two fixing claws fit the protrusions at both ends of the second lighting component. The lighting component is fixed on the fixing claws 46, and the contact part of the frame and the lighting component has a hollow structure, so that light can irradiate the petri dish 40 and the sample. The lighting component can be quickly disassembled and assembled by the fixing claws 46 to meet the different requirements of the lighting in different periods or different test items in the plant cultivation process.

Figure 12:
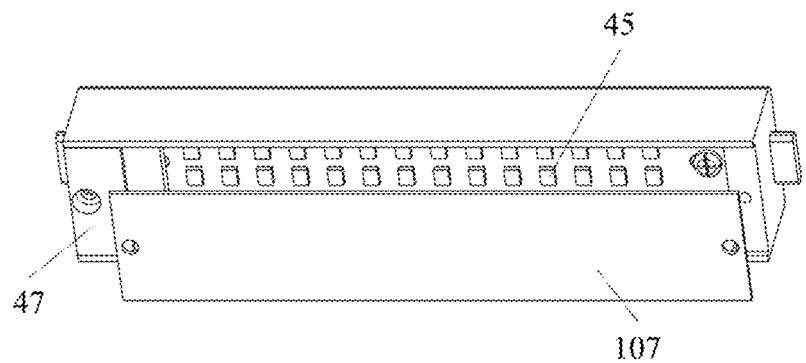
FIG. 12 shows a schematic diagram of an overhead light source according to embodiments of the present disclosure.
Figure 13:
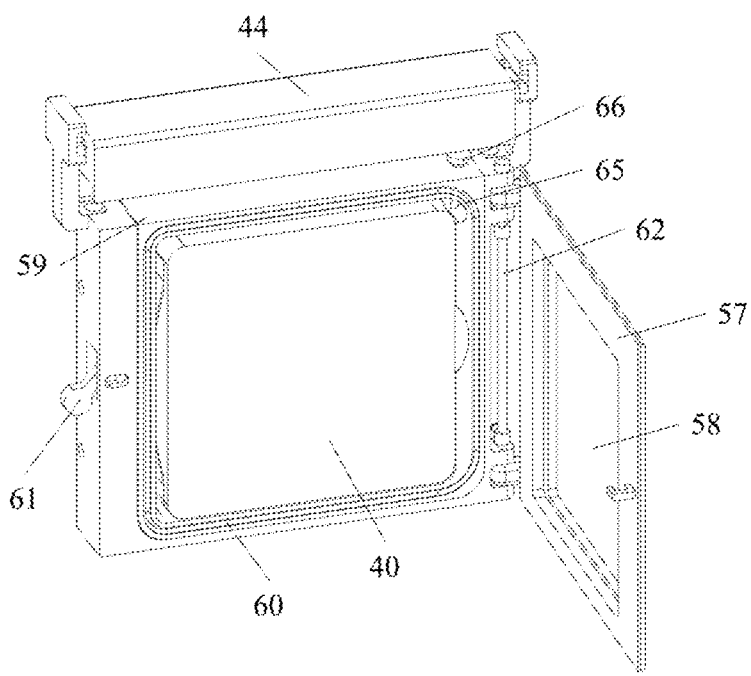
FIGS. 13-16 show schematic diagrams of an airtight petri dish rack according to embodiments of the present disclosure.
Figure 14:
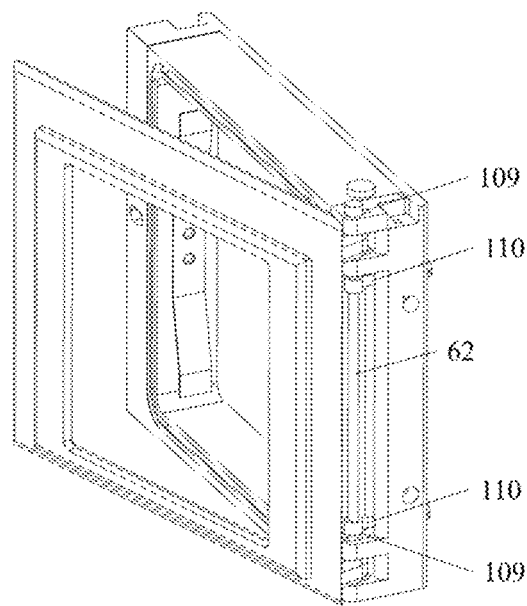
Figure 15:
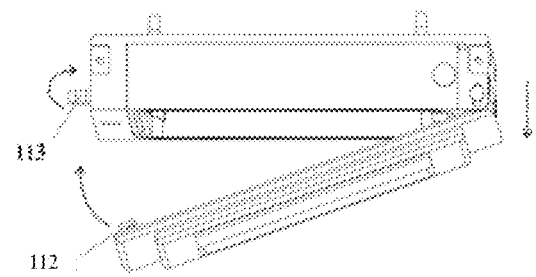

According to embodiments of the present disclosure, the first lighting component and the second lighting component may include an LED aluminum substrate, for example, the LED aluminum substrate 45 as shown in FIG. 12. A plurality of lamp beads are arranged on the LED aluminum substrate. At least two of white light, red light, far red light, blue light, ultraviolet light, and green light sources are combined and packaged in the lamp beads, which can provide a variety of light sources of different wavelengths of far red light, red light, green light, blue light, white light, ultraviolet light, etc. The first lighting component and the second lighting component are connected to the electrical socket interface 34 on the second bracket through a power supply cable, and the on-off and light intensity of each light can be individually controlled by the control circuit of the device. A variety of monochromatic lights, especially the wavelengths that may be turned on at the same time, such as red light, far red light, blue light, etc., are combined and packaged in a single lamp bead to avoid differences in light source positions and light directions when different wavelengths are turned on, which will affect the consistency of conditions of the experiment. For lights that will not be turned on at the same time, such as white light and each monochromatic light, they can be divided into two groups of lamp beads and arranged alternately to meet the requirements of greater output power. One LED light source for cultivation can control at least 4 different color light sources at the same time.

According to embodiments of the present disclosure, the first lighting component and the second lighting component each include a light homogenizing plate, such as the light homogenizing plate 107 shown in FIG. 12. The light homogenizing plate 107 is arranged on the light propagation path of the light source. The thickness of the homogenizing plate may be, for example, 1~2 mm. According to embodiments of the present disclosure, the second lighting component may be provided with a lampshade fixing groove 47 for mounting the aforementioned light homogenizing plate. By mounting the homogenizing plate on the lighting component, the light can be evenly irradiated to the sample, reducing the experimental error caused by uneven light.

As shown in FIG. 8, the frame, the back cover, and the fixing component are each provided with a filter mounting groove on the side close to the petri dish 40 for mounting the filter, such as the top groove 49 and the front groove 50. Since the front and back of the petri dish rack is transparent, when a large number of samples need to be concentrated for research and shooting and recording under light conditions, the light emitted by the lighting component of the petri dish rack can easily interfere with samples near the petri dish rack. Also, due to the reflection of the light emitted by the lighting component by the frame material in the petri dish rack, the light received by the plant is not only in the direction of the lighting component, resulting in errors in the study of the phototropism of the sample. The filters can be selected in different types according to research requirements, such as ultraviolet filters, visible filters, infrared filters, etc.

According to the technical solution provided by embodiments of the present disclosure, the lighting components in the device can irradiate the samples with light of different wavelengths at equal distances to ensure that the distances between the plant samples in each petri dish and the light source are the same, so that the received light intensity remains consistent, so as to maintain the uniformity and repeatability of experimental conditions.

The prior art culture device cannot accurately control the concentration of gas components in the culture device during the sample culture process on the premise of ensuring the tightness. That is, it is difficult to accurately control the concentration of gas components in the culture device during the sample culture process if the tightness of the culture device is guaranteed. If the concentration of gas components in the culture device is accurately controlled, it is difficult to ensure the tightness of the culture device, and it is easy to cause pollution to the internal environment of the culture device. The embodiments of the present disclosure provide an airtight petri dish rack which at least partially solves the above problems. FIGS. 13-18 shows a schematic diagram of an airtight petri dish rack 38 according to embodiments of the present disclosure. As shown in FIGS. 13-18, the airtight petri dish rack 38 comprises:
- a frame with a rotating shaft 62 on one end and a back cover on the back;
- an inner box 59 embedded in the containing space formed by the frame and the back cover for containing the petri dish 40;
- a second front cover 57 rotatably connected with the frame by means of the rotating shaft 62 to realize the opening and closing of the airtight petri dish rack 38.

A groove 60 is provided around the inner box 59, and a sealing component is mounted in the groove 60. The second front cover 57 can be rotated around the rotating shaft 62 to closely contact with the sealing component, at which time the airtight petri dish rack 38 can form an airtight space.

The petri dish 40 is used to hold the sample to be observed. The sample to be observed can be, for example, a plant seedling sample. In this embodiment, the petri dish 40 can be sterilized with ethylene oxide or cobalt-60 radiation before use, and a high-temperature sterilized medium can be placed in the petri dish 40. A sample of the plant seedling is contained in the culture medium.

In embodiments of the present disclosure, the frame has a hollow structure to form an accommodating space with the back cover to accommodate the inner box 59.

In embodiments of the present disclosure, the back cover is made of a transparent material to facilitate observation and shooting of the internal conditions of the airtight petri dish rack 38.

In embodiments of the present disclosure, a long slot 109 is provided at the connection between the frame and the rotating shaft 62, and an elastic component 110 is mounted between the frame and the rotating shaft 62, so that the rotating shaft 62 can move back and forth in the long groove 109 under the force of the elastic component 110. The elastic component 110 may be a spring, for example.

In embodiments of the present disclosure, the sealing component is a sealing component made of elastic material with sealing performance, for example, the sealing component may be a rubber ring.

In embodiments of the present disclosure, the other side of the frame, that is, the side opposite to the rotating shaft 62, is provided with a first fastener 61 or 113. A second fastener 112 is mounted on the side of the second front cover 57 away from the rotating shaft 62. The first fastener 113 can be fastened to the second fastener 112. With the fastening connection between the first fastener 113 and the second fastener 112, the second front cover 57 can be closely attached to the sealing component, so that the airtight petri dish rack 38 forms an airtight space. The first fastener 113 may be, for example, a rotatable wrench, and the second fastener 112 may be a component capable of being hooked, for example, a hook or circle, that can be fastened to the rotatable wrench. The rotatable wrench can be turned and buckle the component capable of being hooked to present a fixed connection state.

Based on the above technical solution, when it is necessary to achieve an inner airtight petri dish rack 38, the second front cover 57 can be stretched out with the rotating shaft 62 as the stress point. That is, the second front cover 57 is stretched toward the outside of the airtight petri dish rack 38 while overcoming the force of the elastic component 110. When the second front cover 57 rotates to come into contact with the sealing component mounted around the inner box 59, the first fastener 113 and the second fastener 112 are fastened and connected, so that the second front cover 57 is closely attached to the sealing component. At this time, through the fastening connection of the first fastener 113 and the second fastener 112, and under the force of the elastic component 110, the second front cover 57 can be tightly pulled toward the frame and the inner body 59, ensuring that the second front cover 57 and the surface of the inner box 59 form a closed space through the sealing component.

In addition, since the airtight petri dish rack 38 is provided with a second front cover, which can form a closed space, the sample petri dish 40 can be directly put into the inner box 59 of the airtight petri dish rack 38 without its own upper cover. Further, since the upper cover of the sample petri dish 40 is omitted, it can effectively avoid the influence of condensation on the upper cover of the sample petri dish 40 during the long-term culturing of the sample on the imaging of the sample to be observed, and it can also significantly improve the detail resolution of the sample to be imaged.

In embodiments of the present disclosure, the second front cover 57 is also provided with a light-transmitting observation window to observe the sample to be observed placed in the sample petri dish 40, and to keep it airtight. Further, in embodiments of the present disclosure, the observation window is covered with double-sided coated glass 58 to enhance the transmittance of the visible light band and the 940 nm infrared light band.

Figure 16:
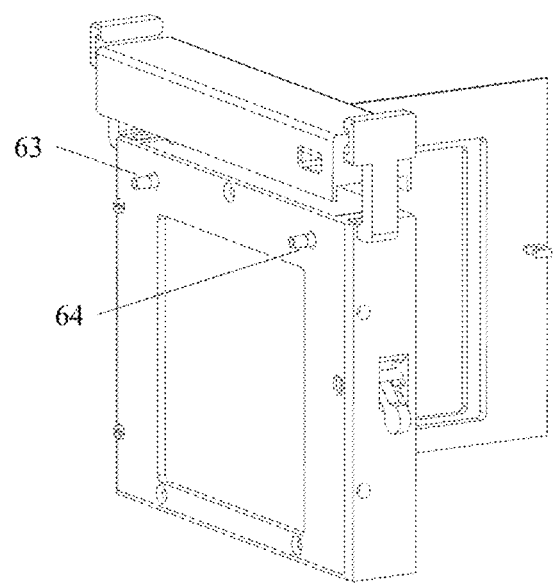

As shown in FIG. 16, in embodiments of the present disclosure, the back of the inner box 59 is provided with an inlet opening 63 and an outlet opening 64, wherein the inlet opening 63 is connected to an external air pump for pumping external air into the airtight petri dish rack 38. An air filter component, such as a filter membrane with a pore size of 0.22 μm, can be arranged in the air path of the pumped air to filter microorganisms in the input air, so that the air that pumped into the airtight petri dish rack 38 is sterile. The outlet opening 64 is used to exhaust the air in the airtight petri dish rack 38.

During the operation process, the air is continuously pumped in through the inlet opening 63, and discharged through the outlet opening 64 to relieve the pressure, so that the air pressure inside the airtight petri dish rack 38 is always slightly higher than the outside, which can prevent bacterial air entering from the outside so as to ensure that the inside of the airtight petri dish rack 38 is always in a sterile environment. In addition, because the air pump can quickly exchange the air components inside the airtight petri dish rack 38 with outside air components, and the sample to be observed is directly exposed to the air inside the airtight petri dish rack 38, therefore, when it is necessary to use other control devices to adjust the gas component concentration inside the airtight petri dish rack 38, the sample to be observed can quickly feel the change in the gas component concentration.

It should be noted that the gas flow rate pumped into the airtight petri dish rack 38 can be set according to actual application requirements. For example, for a plant sample to be observed with a culture medium, the gas flow rate of the gas that pumped into the airtight petri dish rack 38 should be controlled at about 30~100 mL/min. If the gas flow rate is too high, it is easy to cause the culture medium to dry up. If the gas flow rate is too low, it is not favorable to the quick balance of the internal environment of the airtight petri dish rack 38 and the external environment.

Figure 17:
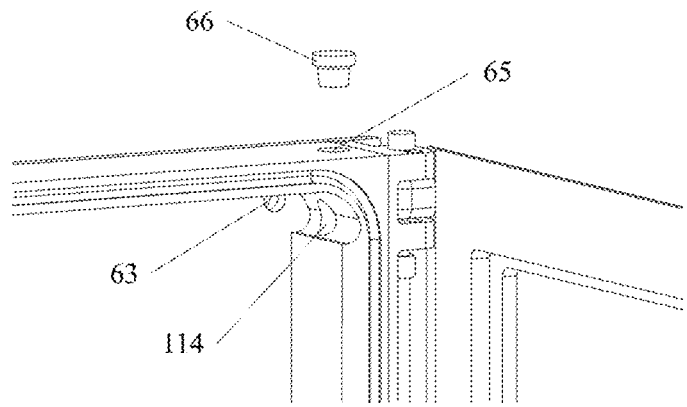
FIG. 17 shows a structural schematic diagram of the top of the frame according to embodiments of the present disclosure.

FIG. 17 shows a schematic structural view of the top of the frame according to embodiments of the present disclosure. As shown in FIG. 17, in embodiments of the present disclosure, a water storage tank 65 is provided at the top of the frame near the inlet opening 63 for sterile water, wherein a water delivery hole 114 is opened into the inner box 59 on the side wall of the water storage tank 65 for guiding the sterile water stored in the water storage tank to the inner box 59. After the drained water volatilizes, it can be brought into the inner box 59 by the gas pumped in through the inlet opening 63, so as to increase the humidity of the air inside the inner box 59 and slow down the evaporation of water in the sample medium to be observed, and prevent the evaporation of water and the drying up of the sample medium to be observed due to long-term ventilation.

In embodiments of the present disclosure, the water storage tank 65 is further equipped with a water tank cover 66, for example, a T-shaped water tank cover as shown in FIG. 17. After the sterile water is introduced into the water storage tank 65, the water tank cover 66 can be covered to prevent the sterile water in the water storage tank 65 from being contaminated by microorganisms in the outside air.

Figure 18:
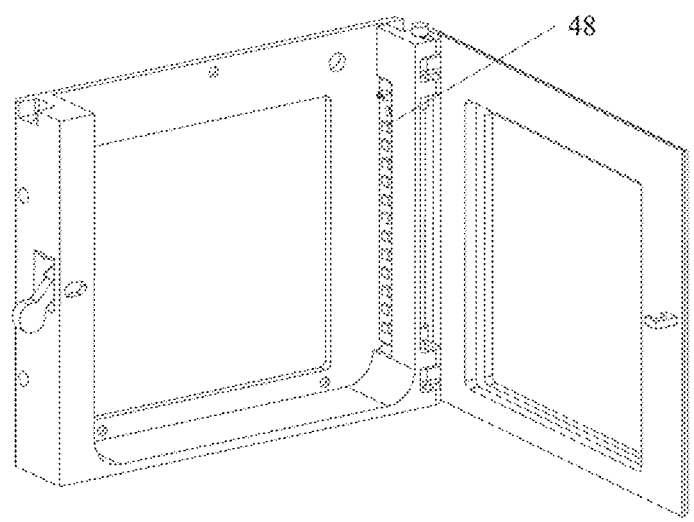
FIG. 18 shows a schematic diagram of a side light source according to embodiments of the present disclosure.

The existing equipment cannot guarantee that every plant in a large-scale experiment can be subjected to the illumination of the same distance, angle and intensity. Since light is a very important factor in the process of plant growth, the intensity, angle, and wavelength of the light can all directly affect plant growth. Therefore, in embodiments of the present disclosure, a first lighting component 48 may be mounted on the side of the frame, for example, the side of the frame close to the rotating shaft 62, in the space between the inner box 59 and the external device, as shown in FIG. 18, to change the light direction felt by the sample to be observed, and to be used to study the phototropic response of plants. The first lighting component 48 can be fixed on the frame by screws or buckles. In embodiments of the present disclosure, a second lighting component 44 may be mounted on the top of the frame to provide a light source for the sample to be observed, and the airtight petri dish rack 38 may further include at least two fixing claws 50. In embodiments of the present disclosure, a filter mounting groove is arranged on the inner surface of the frame close to the back of the sample petri dish 40 for mounting the filter. The first lighting component, the second lighting component, the fixing claws, the filter mounting groove, etc. are similar to the foregoing description of the small vertical petri dish rack or the large horizontal petri dish rack, which will not be repeated here.

In embodiments of the present disclosure, in order to allow the light emitted by the lighting component to pass through the inner box 59, the inner box 59 is made of a transparent material, for example, a transparent acrylic material.

In embodiments of the present disclosure, the frame or both ends of the back surface of the back cover can be provided with fixing holes to connect with the rotating frame, wherein the rotating frame can be connected with a plurality of the airtight petri dishes rack 38 to realize simultaneous observation of a large number of samples to be observed.

At present, some gravitational studies on plant seedlings rely on the weightless environment. For example, in a paper published by Paul et al. in 2012, through experiments on the International Space Station, they studied the growth direction of root tips of *Arabidopsis* seeds after germination under weightless conditions. However, the cost of this research method is too high for ordinary research teams to reproduce.

In order to solve the problems in the related art, embodiments of the present disclosure provide a petri dish rack, which includes a base, a turntable and a servo motor fixed on the base, wherein the turntable is provided with a fixing device, and the servo motor is connected with the turntable, so that the petri dish can be mounted on the turntable by the fixing device. The turntable is driven by the servo motor to rotate, thereby controlling the rotation of the petri dish, which can realize the change of the direction of gravity, and even simulate a weightless environment by disturbing the direction of gravity.

Figure 19:
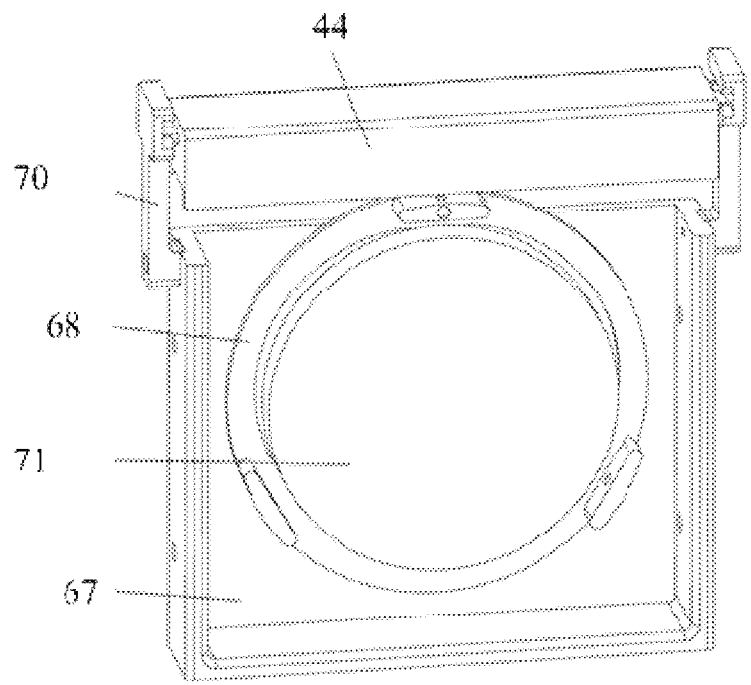
FIGS. 19 and 20 show schematic diagrams of a gravity petri dish rack according to embodiments of the present disclosure.
Figure 20:
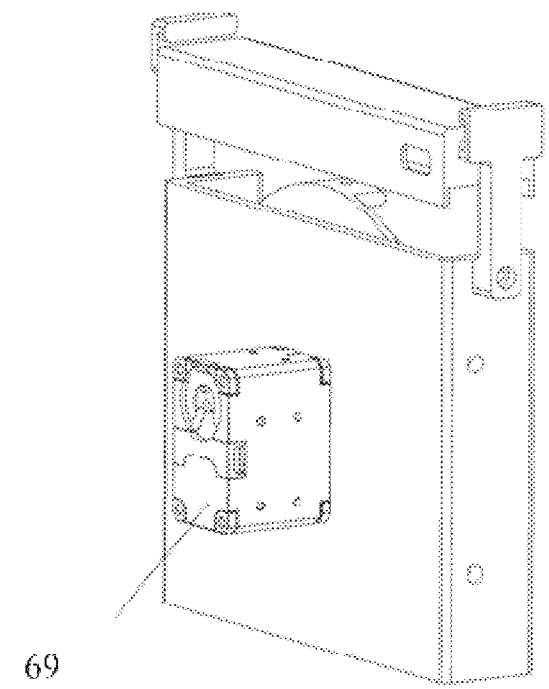

FIG. 19 and FIG. 20 show schematic diagrams of a gravity petri dish rack according to embodiments of the present disclosure.

As shown in FIG. 19 and FIG. 20, the gravity petri dish rack includes: a second base 67; a turntable 68 fixed on the second base 67, and provided with a fixing device; and a servo motor 69 fixed on the second base 67 and connected to the turntable 68.

According to embodiments of the present disclosure, the center of the turntable 68 is connected to the servo motor 69, the servo motor 69 is fixed on the second base 67, and the fixing device is configured to fix the petri dish 71. By sending a signal to the servo motor 69 through a control circuit, the turntable 68 can be controlled to drive the petri dish 71 to rotate a fixed angle to change the direction of gravity, or to continuously rotate at a certain speed to simulate a weightless state. The petri dish 71 may be a general round petri dish.

According to embodiments of the present disclosure, two fixing holes are provided on opposite sides of the second base. The interval between the fixing holes is matched with the rotating frame described above, and is used to mount the gravity petri dish rack on the rotating frame, occupying one rack position of the rotating frame.

According to embodiments of the present disclosure, the fixing device may include, for example, a screw or a spring clip, configured to fix the petri dish 71. The fixing device may also comprise at least three sets of spring baffles, which can move in the plane where the turntable is located, and can provide pressure in the center direction of the turntable under the action of the spring. According to embodiments of the present disclosure, the petri dish 71 can be placed on the turntable 68 by pulling apart the spring baffle, the angle between the spring baffle and the turntable can be less than 90°, and the spring baffle provides pressure inward to fix the petri dish 71 to prevent displacement during use.

According to embodiments of the present disclosure, the gravity petri dish rack may further be provided with a first lighting component, a second lighting component 44, a fixing claw 70, etc., which can be understood with reference to the above description, and will not be repeated here.

The gravity culture petri rack as described in FIG. 19 and FIG. 20 is detachably mounted between the two adjacent second brackets 32, and the wiring of the servo motor 69 is connected to the electrical socket interface 34. According to embodiments of the present disclosure, the wiring of the first lighting component or the second lighting component may also be connected to the electrical socket interface 34.

Embodiments of the present disclosure provides a control method for controlling the petri dish rack described above, including: obtaining an angle information; and controlling the servo motor to drive the turntable to rotate to a target position according to the angle information.

The following is an example to illustrate the experimental method by studying the gravitropism response of the roots of *Arabidopsis* seedlings:

a) Surface sterilization of *Arabidopsis* seeds: place a suitable amount of seeds in a 1.5 mL centrifuge tube, soak in 75% alcohol+0.01% Triton X-100 and fully shake for 10 minutes, then pour out the liquid; rinse with 95% alcohol, and pour out the liquid; dry thoroughly in an open state in the clean bench, then close the tube cap tightly.

b) Medium configuration: use 4.33 g/L Murashige-Skoog salt mixture, 10 g/L sucrose, 8 g/L Phytagel plant gel, add deionized water to prepare 1 L culture medium, use KOH and HCl to adjust the pH to 5.7~5.8; sterilize at 121° C. for 15 minutes, cool to about 60° C., pour it into a sterile transparent round plastic petri dish with a diameter of about 90 mm in a clean bench. The thickness of the culture medium is about 3 to 4 mm. Set the culture medium aside for cooling and solidification. In embodiments of the present disclosure, Phytagel is used as the coagulant for the culture medium, which is more transparent than agar and is convenient to obtain higher imaging clarity.

c) Sowing and seed germination: use tweezers to sow the sterilized seeds on the surface of the culture medium in the clean bench, and arrange them in a row with an interval of about 5 mm; cover the petri dish lid and seal it with a sealing film; place it in environment of 4° C. away from light after swelling for 4 days, take it out and place it upright and cultivate it under 22° C. light for 5 days. The *Arabidopsis* seedlings should grow upright against the surface of the medium.

d) Mounting the gravity petri dish rack: screw four M6*12 hex screws into the fixing holes on both sides of the second base 67 of the gravity petri dish rack, slide them into the mounting holes on the rotating frame and tighten them, insert the wiring of the servo motor 69 and the culture light source 44 into the electrical socket interface 34.

e) Sample loading: remove the sealing film of the petri dish, and fix it on the turntable 68 with the back facing outward and the cover facing inward to avoid the interference of condensation on the front cover; insert a layer of black flocking cloth or hard paper coated with black light-absorbing paint between the petri dish and the turntable to improve the contrast between the plant sample and the background when shooting.

f) Start each module of the biological sample imaging device: control the closed incubator 4 through computer software to provide a 22° C. constant temperature environment in the incubator; continuously provide fresh air to the incubator; control the overhead light source 44 to provide mixed white light illumination; turn on the front infrared imaging lighting module on the imaging module, use 940 nm infrared light to provide illumination from the side of the sample; control the imaging module and the rotating frame to perform continuous dynamic imaging of the petri dishes on each gravity petri dish rack, that is, move the camera position of the imaging module and rotate the rotating frame every set time interval (such as 5 min), and take a round of shooting for each petri dish.

g) Change the direction of gravity: at the predetermined time of the experiment, control the servo motors on each gravity petri dish rack through the computer software, read their current positions respectively, calculate the position value after 90° clockwise rotation, and move them to the corresponding positions respectively. If a round of shooting of all sample has not been completed at the predetermined time of the experiment, wait for the completion of the round of sample shooting before operating the servo motor.

h) Continue to perform continuous dynamic imaging until the predetermined time of the experiment; analyze the acquired image data to study the effect of the change of gravity direction on the growth direction of *Arabidopsis* roots.

In addition, the gravity petri dish rack provided by embodiments of the present disclosure can continuously change the gravity direction relative to the plant by continuously rotating, disturbing the influence of gravity on the plant, so as to simulate a weightless environment. Using the real-time dynamic imaging of this device, the response changes of plant seedlings to gravity can be observed and analyzed.

According to embodiments of the present disclosure, the control method of the gravity petri dish rack may include: controlling the servo motor to drive the turntable to continuously rotate; in response to obtaining a first control instruction, determining a target angle from at least two candidate angles; and controlling the turntable to stop at the target angle.

According to embodiments of the present disclosure, the servo motor drives the turntable and the petri dish to continuously rotate in the vertical plane, which can disturb the influence of gravity on the plant sample in the petri dish to simulate a weightless environment.

According to embodiments of the present disclosure, the first control instruction, for example, may be generated based on a photographing instruction for controlling the servo motor to stop rotating, so that the turntable and the petri dish stop rotating, so as to improve the sharpness of photographing. Alternatively, after a predetermined time, the turntable may be controlled to continue rotating in response to obtaining a second control instruction.

According to embodiments of the present disclosure, at least two candidate angles, such as 0° and 180°, may be set in advance. Alternatively, more candidate angles, such as 0°, 120°, and 240°, may be set. In response to obtaining the first control instruction, the turntable is controlled to stop at one of the candidate angles, that is, the target angle. Since there are more than two candidate angles, it will not stop at the same position every time when photographing, which reduces the cumulative effect of gravity during the photographing.

For example, when the number of turntable stops is an odd number, it stops at the first angle among the candidate angles, such as 0°; when the number of turntable stops is an even number, it stops at a second angle different from the first angle among the candidate angles, such as 180°.

Those of ordinary skill in the art should know that the second angle can be other angles different from 180 degrees. Alternatively, three, four or more candidate angles, or random angles, can be preset, thereby reducing the cumulative effect of gravity during the photographing to better simulate the weightlessness environment, which is not limited in the present disclosure.

According to embodiments of the present disclosure, the image is captured after the servo motor is paused. Since the angle of the turntable is different during the pause, the orientation of the petri dish in the exposed image is also different. Image feature recognition, that is, the affine transformation method can be used to align images and correct all images to a uniform orientation.

Those of ordinary skill in the art should know that other methods can also be used to perform image alignment and correct to a uniform orientation, which is not limited in the present disclosure.

According to the technical solution provided by embodiments of the present disclosure, the turntable is driven to continuously rotate by controlling the servo motor. In response to obtaining the first control instruction, a target angle is determined from at least two candidate angles, and the turntable is controlled to stop at the target angle, which can improve the sharpness of photographs while reducing the cumulative effect of gravity. On the other hand, stopping and shooting at a predetermined candidate angle is favorable to post-image alignment and analysis.

The following is an example of studying the mechanism of *Arabidopsis* seedling development influenced by gravity.

a) Surface sterilization of *Arabidopsis* seeds: place an appropriate amount of *Arabidopsis* seeds in a 1.5 mL centrifuge tube, soak in 75% alcohol+0.01% Triton X-100 and fully shake for 10 minutes, pour out the liquid; rinse with 95% alcohol and pour out the liquid; dry thoroughly in an open state in a clean bench and close the tube cap tightly.

b) Medium configuration: use 4.33 g/L Murashige-Skoog salt mixture, 10 g/L sucrose, 8 g/L Phytagel plant gel, add deionized water to prepare 1 L culture medium, use KOH and HCl to adjust the pH to 5.7~5.8; sterilize at 121° C. for 15 minutes, cool to about 60° C., pour it into a sterile transparent round plastic petri dish with a diameter of about 90 mm in the clean bench, the thickness of the culture medium is about 3 to 4 mm; set aside for cooling and solidification.

c) Sowing and seed germination: use tweezers to sow the sterilized seeds on the surface of the culture medium in a clean bench, and arrange them in a row with an interval of about 5 mm; cover the petri dish lid and seal it with a sealing film; place it in environment of 4° C. away from light after swelling for 4 days, take it out for photographing.

d) Mounting the gravity petri dish rack: mount the gravity petri dish rack on the rotating frame 5 through the fixing holes on both sides of the second base 67 of the gravity petri dish rack, and insert the wiring of the servo motor 69 and the overhead culture light source 44 into the electrical socket interface 34.

e) Sample loading: remove the sealing film of the petri dish to reduce interference of condensation on the front cover and promote internal and external gas exchange, and fix the petri dish on the turntable 68 with the back facing outward and the cover facing inward; insert a layer of black flocking cloth or hard paper coated with black light-absorbing paint between the petri dish and the turntable to improve the contrast between the plant sample and the background when shooting.

f) Start each module of the biological sample imaging device: control the incubator 4 through computer software to provide a 22° C. constant temperature environment in the incubator; continuously provide fresh air to the incubator; control the overhead light source 44 to provide mixed white light illumination; turn on the front infrared imaging lighting module, use 940 nm infrared light to provide illumination from the front side of the sample; control the imaging module to perform continuous dynamic imaging of the petri dishes on each gravity petri dish rack, that is, move the camera position of the imaging module and rotate main bracket every set time interval (such as 5 min), and take a round of shooting for each petri dish.

g) Simulate weightless environment: from the beginning of the experiment, the servo motor 69 is controlled by computer software to continuously rotate clockwise, and the speed is controlled at 5-15 revolutions/min. It should not be too fast to weaken the influence of radial acceleration on plant growth to avoid systemic errors, and should not be too slow to weaken the effect of gravity interference. When shooting is needed, the camera of the imaging module and the rotating frame are moved to the corresponding target position. The rotation position of the servo motor corresponding to the petri dish to be shot is controlled, and the servo motor stops when rotating to 0° in the odd number of shooting rounds, and stops when rotating to 180° in the even number of shooting rounds, and the other servo motors continue to rotate. The camera immediately exposes and shoots when the servo motor stops, and immediately restarts the rotation of the corresponding servo motor after the exposure is completed, the direction and speed are the same as before.

h) Continue to perform continuous dynamic imaging until the predetermined time of the experiment; statistically analyze the growth direction of the root tip and hypocotyl after seed germination.

Figure 21A:
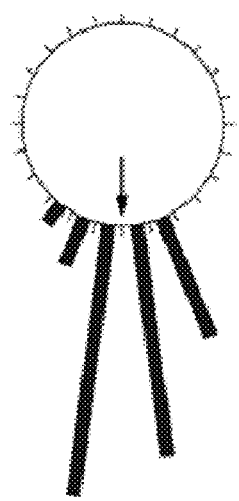
FIG. 21A shows the distribution of plant root tip directions under normal culture conditions.
Figure 21B:
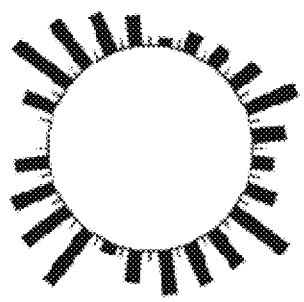
FIG. 21B shows a schematic diagram of the distribution of plant root tip directions under the condition of gravitational disturbance according to embodiments of the present disclosure.

FIG. 21A shows a schematic diagram of the direction distribution of plant root tip under normal culture conditions. FIG. 21B shows a schematic diagram of the direction distribution of plant root tips under conditions of gravity disturbance according to embodiments of the present disclosure, wherein the length of the bars in the figure represents the proportion of roots in respective directions, and the arrow in FIG. 21A indicates the direction of gravity.

Embodiments of the present disclosure can effectively reduce the cumulative effect of gravity in a certain direction. Under normal gravity conditions, as shown in FIG. 21A, the root tip direction of *Arabidopsis* seedlings is concentrated in the vertical direction. However, under the condition of simulating weightlessness in embodiments of the present disclosure, as shown in FIG. 21B, the root tip directions are uniformly distributed in various directions, and the experimental results are consistent with the growth status of plant seedlings in the International Space Station reported by Paul et al. in 2012, which verifies the effectiveness of this method in simulating a weightless environment. Therefore, the technical solutions of embodiments of the present disclosure can simulate a weightless environment in space in the ground environment, and provide feasible methods on the ground for the botany research that must be carried out on the space station in the past.

The biological sample cultivation module 5 of embodiments of the present disclosure has been described above, and the imaging module 3, the three-dimensional displacement control device, and the lighting device of embodiments of the present disclosure will be described below.

The prior art can only control the camera to move in the horizontal and vertical directions. Due to the limited depth of field of the lens, it is impossible to effectively realize the real-time change of positions among a large number of samples, thereby reducing the shooting efficiency of the sample observation image and reducing the shooting throughput.

In the technical solution provided by embodiments of the present disclosure, the imaging module is arranged on a three-dimensional displacement control device through an adapter assembly. The adapter assembly has a horizontal platform surface which is provided with a guide rail and a positioning pin hole The guide rail is configured to provide a sliding path. The positioning pin hole is configured to position the imaging module.

Figure 22:
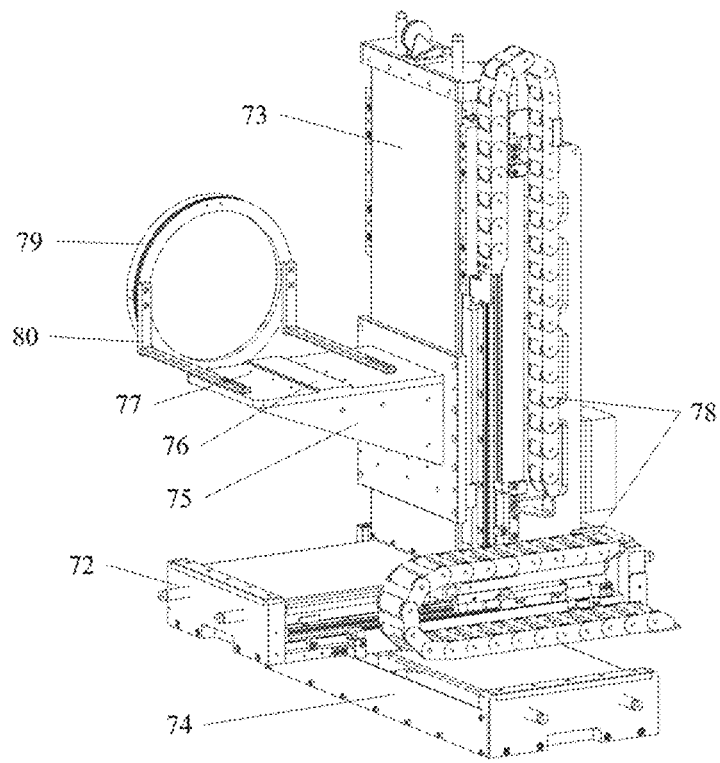
FIG. 22 shows a schematic diagram of a three-dimensional displacement control device according to embodiments of the present disclosure.

FIG. 22 shows a schematic diagram of a three-dimensional displacement control device according to embodiments of the present disclosure. As shown in FIG. 22, the three-dimensional displacement control device includes a horizontal displacement component 72, a vertical displacement component 73, and a depth displacement component 74.

The horizontal displacement component 72, a vertical displacement component 73 and a depth displacement component 74 are connected.

The horizontal displacement component 72 is mounted in the horizontal direction, and is used to drive the imaging module of the displacement control device to be displaced in the horizontal direction, and to control the displacement of the imaging module in the horizontal direction.

The vertical displacement component 73 is mounted in the vertical direction, and is used to drive the imaging module to be displaced in the vertical direction, and to control the displacement of the imaging module in the vertical direction.

The depth displacement component 74 is mounted in the depth direction, and is used to drive the image bearing module to be displaced in the depth direction, and to control the displacement of the image bearing module in the depth direction.

According to the technical solution provided by embodiments of the present disclosure, the displacement control device with the displacement components in three dimensions is provided to realize the displacement movement of the imaging component in three directions of horizontal, vertical and depth. This avoids the facts that the imaging component cannot effectively change the position between a large number of samples in real time, and cannot accurately focus and collect the images of the shot samples at different positions due to the limited depth of field of the imaging component lens, thereby greatly improving the sample observation image shooting efficiency and increasing the shooting throughput.

In embodiments of the present disclosure, the horizontal displacement component 72, the vertical displacement component 73, and the depth displacement component 74 may be connected in various ways. For example, as shown in FIG. 22, the depth displacement component 74 is connected to the horizontal displacement component 72, and the horizontal displacement component 72 is connected to the vertical displacement component 73. Alternatively, the depth displacement component 74 is connected to the vertical displacement component 73, and the vertical displacement component 73 is connected to the horizontal displacement component 72. Alternatively, the horizontal displacement component 72 is connected to the vertical displacement component 73, and the vertical displacement component 73 is connected to the depth displacement component 74. Alternatively, the horizontal displacement component 72 is connected to the depth displacement component 74, the depth displacement component 74 is connected to the vertical displacement component 73. Alternatively, the vertical displacement component 73 is connected to the horizontal displacement component 72, and the horizontal displacement component 72 is connected to the depth displacement component 74. Alternatively, the vertical displacement component 73 is connected to the depth displacement component 74, and the depth displacement component 74 is connected to the horizontal displacement component 72, and so on. It should be noted that the various possible connections between the horizontal displacement component 72, the vertical displacement component 73 and the depth displacement component 74 can be adopted as long as the horizontal displacement component 72, the vertical displacement component 73 and the depth displacement component 74 can be connected as a whole and can perform independent displacement movement respectively. The present disclosure does not specifically limit the connection mode among the horizontal displacement component 72, the vertical displacement component 73 and the depth displacement component 74. For the convenience of description, the following takes the connection mode shown in FIG. 22, where the depth displacement component 74 is connected to the horizontal displacement component 72, and the horizontal displacement component 72 is connected to the vertical displacement component 73, as an example.

In embodiments of the present disclosure, the horizontal displacement component 72, the vertical displacement component 73 and/or the depth displacement component 74 are all linear displacement components, that is, the horizontal displacement component 72, the vertical displacement component 73 and/or the depth displacement component 74 can move along a straight line.

In embodiments of the present disclosure, the displacement control device further includes one or more driving components connected to the horizontal displacement component 72, the vertical displacement component 73, and the depth displacement component 74 for driving the horizontal displacement component 72, the vertical displacement component 73 and the depth displacement component 74 to perform displacement movement. The driving component may be a motion driving component such as a stepper motor/screw guide rail or a direct drive motor. When there is one driving component, it can be connected to the horizontal displacement component 72, the vertical displacement component 73, and the depth displacement component 74 at the same time. When there are a plurality of driving components, the plurality of driving components can be respectively connected to the horizontal displacement component 72, the vertical displacement component 73 and the depth displacement component 74.

In embodiments of the present disclosure, the displacement control device further includes an encoder, which is connected to the horizontal displacement component 72, the vertical displacement component 73 and/or the depth displacement component 74, and is configured to utilize a feedback control mechanism to accurately control the displacement movement of the horizontal displacement component 72, the vertical displacement component 73 and/or the depth displacement component 74 so as to improve the movement and positioning accuracy of the horizontal displacement component 72, the vertical displacement component 73 and/or the depth displacement component 74. The feedback control mechanism of the encoder is a common technique in the prior art, and detailed description thereof is omitted in this disclosure.

In embodiments of the present disclosure, the horizontal displacement component 72, the vertical displacement component 73, and/or the depth displacement component 74 may also be attached with photoelectric limit switches to perform zero position calibration for the horizontal displacement component 72, vertical displacement component 73 and/or depth displacement component 74.

In embodiments of the present disclosure, the principle for using the photoelectric limit switch to perform zero position calibration on the horizontal displacement component 72, the vertical displacement component 73 and/or the depth displacement component 74 is as follows.

First, the displacement component is controlled to move at a first speed, such as about 10 mm/s, toward a negative limit direction, until the photoelectric limit switch signal is triggered, and then stops moving.

Then, the displacement component is controlled to move at a second speed, such as about 10 mm/s, toward a positive limit direction a first preset distance at a time, such as 50 μm, until the photoelectric limit switch signal disappears, and then stops moving.

Then, the displacement component is controlled to move slowly at a third speed, such as about 1 mm/s, toward the negative limit direction, until the photoelectric limit switch signal is triggered, and then stops moving.

Finally, the displacement component is controlled to move at a fourth speed, such as a normal driving speed, toward the positive limit direction a second preset distance, such as 2 mm, and set the current position as the zero position of the displacement component.

In embodiments of the present disclosure, the displacement control device further includes an adapter assembly 75 that is mounted on the horizontal displacement component 72, the vertical displacement component 73 or the depth displacement component 74 for a carrying object. The adapter assembly 75 has a horizontal surface provided with a guide rail 76 and one or more positioning pin holes 77. The guide rail 76 is used to provide a sliding path of the carrying object, so that the carrying object moves along the guide rail 76 and slides to a suitable position on the surface of the adapter assembly. The positioning pin holes 77 can be used to position and fix the carrying object so that the carrying object can move with the displacement component along with the displacement component where the adapter assembly 75 is mounted.

In embodiments of the present invention, the cross section of the guide rail 76 is dovetail or inverted trapezoid, so that the carrying object can be mounted or replaced safely and quickly. In addition, the upper surface of the guide rail 76 may be higher than the upper surface of the adapter assembly, that is, protruding on the adapter assembly; or lower than the upper surface of the adapter assembly, that is, recessed on the adapter assembly. The present disclosure does not specifically limit the mounting method and mounting direction of the guide rail 76 on the horizontal surface of the adapter assembly, as long as the carrying object can safely slide on the guide rail 76 without leading the displacement component to cause obstacles or conflicts to the sliding and working of the carrying object. For example, if the carrying object is an imaging component such as a camera, and the displacement components are arranged and connected as shown in FIG. 22, the adapter assembly 75 is mounted on one side of the vertical displacement component 73, then the mounting direction of the guide rail 76 on the horizontal surface of the adapter assembly can be parallel to the depth displacement component 74, thereby avoiding collide or conflict with the movement of other displacement components when the carrying object slides on the horizontal surface of the adapter assembly by means of the guide rail 76.

In embodiments of the present disclosure, the displacement control device further includes a towline 78. The towline 78 is a chain-shaped component with an accommodation space, and there may be one or more towline s. The towline 78 is mounted on the side or non-working surface of the displacement component, and is used to accommodate and fix the connecting lines between the above-mentioned components, so as to avoid scratching or hooking of the connecting lines during the displacement movement, thereby improving the connection stability of the displacement control device. When there are a plurality of tow chains 78, the plurality of tow chains 78 can be mounted on the side of the same displacement component or on the sides of different displacement components.

In embodiments of the present disclosure, the displacement control device further includes a connecting piece 80 which is mounted on the adapter assembly 75. For example, the connecting piece 80 can be fixedly mounted on the horizontal surface of the adapter assembly 75 to be used for fixing the front light source 79. The front light source 79 is separately described in the following, and the description will not be presented in detail here. It should be noted that the present disclosure does not specifically limit the mounting position of the connecting piece 80 on the adapter assembly 75, as long as the connecting piece 80 can connect the front light source 79 with the adapter assembly 75.

In the embodiment of the present invention, the connecting piece 80 may be made of a solid material or a flexible material, that is, the connecting piece 80 may be a solid connecting piece or a flexible connecting piece. When the connecting piece 80 is a flexible connecting piece, the connecting piece 80 can adjust the position and direction of the front light source 79 by its flexible feature, so as to provide a light source of required intensity for the carrying object.

In embodiments of the present disclosure, the displacement control device further includes a controller, which is connected to the horizontal displacement component 72, the vertical displacement component 73, the depth displacement component 74, and the driving component and/or the encoder, so as to control the horizontal displacement component 72, the vertical displacement component 73, the depth displacement component 74, and the driving component and/or the encoder.

Figure 23:
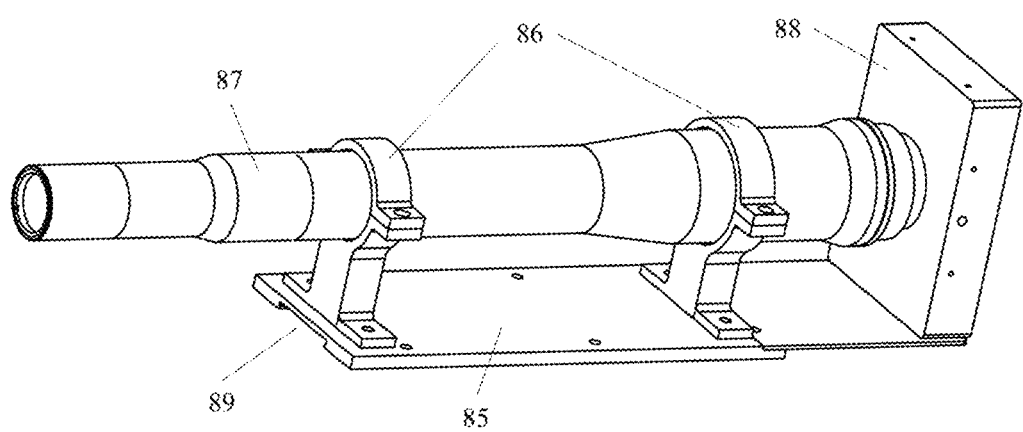
FIG. 23 shows a schematic diagram of a microscopic phenotype detection module according to embodiments of the present disclosure.

According to embodiments of the present disclosure, the imaging module 3 may include any one of a microscopic phenotype detection module, a macroscopic phenotype detection module, a luminescence detection module, and a fluorescence detection module FIG. 23 shows a schematic diagram of a microscopic phenotype detection module according to embodiments of the present disclosure.

As shown in FIG. 23, the microscopic phenotype detection module includes a third base 85, a lens holder 86, a telecentric lens 87, and a first camera 88. The third base 85 has a dovetail groove 89, which can be mounted on the guide rail 76 on the adapter assembly, and can be quickly removed and replaced with other camera modules.

According to embodiments of the present disclosure, a telecentric lens with a magnification of 0.5 to 5 times can be used to photograph the local characteristics of a plant seedling sample according to the size of the sample taken. The higher the magnification, the narrower the lens field of view, the higher the physical resolution. The telecentric lens has the characteristics of small lens distortion and constant size of the out-of-focus contour, which is suitable for measuring length.

According to embodiments of the present disclosure, an 850 nm long-pass filter can be added to the front end of the lens or between the lens and the camera to allow only infrared light with a wavelength above 850 nm to pass. The filter can avoid the influence of the overhead culture light source 44 or the side culture light source 48 on the imaging illumination.

Figure 24:
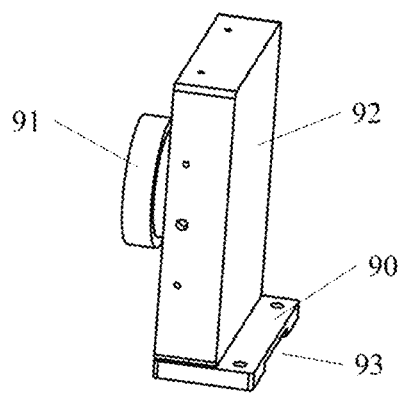
FIG. 24 shows a schematic diagram of a macroscopic phenotype detection module according to embodiments of the present disclosure.

FIG. 24 shows a schematic diagram of a macroscopic phenotype detection module according to embodiments of the present disclosure.

As shown in FIG. 24, the macroscopic phenotype detection module includes a fourth base 90, a first fixed focus lens 91, and a second camera 92 connected together. The dovetail groove 93 of the fourth base can be mounted on the guide rail 76 on the adapter assembly, and can be quickly removed and replaced with other camera modules.

According to embodiments of the present disclosure, the macroscopic phenotype detection module can be used to photograph the entire petri dish in one image, using a fixed-focus lens with a focal length of 15-135 mm, and a magnification between 0.05-0.5 times.

According to embodiments of the present disclosure, an 850 nm long-pass filter can be added to the front end of the lens or between the lens and the camera, allowing only infrared light with wavelengths above 850 nm to pass. The filter can avoid the influence of the overhead culture light source 44 or the side culture light source 48 on the imaging illumination.

Figure 25:
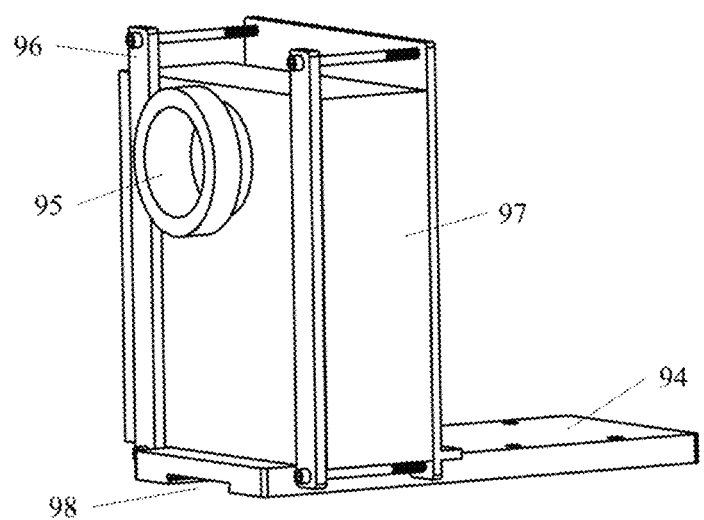
FIG. 25 shows a schematic diagram of a luminescence detection module according to embodiments of the present disclosure.

FIG. 25 shows a schematic diagram of a luminescence detection module according to embodiments of the present disclosure.

According to embodiments of the present disclosure, the reporter gene fused with luciferase is expressed in plants by transgenic or other methods. The substrate luciferin is added to the culture medium, and the luciferase fused to the reporter gene can catalyze the substrate to emit light signals.

The intensity of the light signal represents the expression level of luciferase, that is, the expression of the gene to be studied.

As shown in FIG. 25, the luminescence detection module includes a fifth base 94, a second fixed-focus lens 95, a camera fixing frame 96, and a third camera 97, which are connected together. Among them, the second fixed focus lens 95 may be a large aperture fixed focus lens; the third camera 97 may be a cooled camera. The dovetail groove 98 of the fifth base 94 can be mounted on the guide rail on the adapter assembly 76, and can be quickly removed and replaced with other camera modules.

According to embodiments of the present disclosure, the module is suitable for detecting the luminescence signal generated by the reaction of luciferase and the substrate, such as light with wavelength of 500-560 nm, but not limited to this. The location and level of corresponding gene expression in plants are characterized by the position and intensity of the light signal. As long time exposure is required to detect dim signals, a large aperture lens with an aperture F value of less than 2.0 should be used, and a CCD or CMOS camera with cooling capability should be used.

According to embodiments of the present disclosure, in order to avoid the electromagnetic interference generated during the operation of the direct drive motor of the three-dimensional linear displacement control module causing camera control errors, the cooling camera housing may be additionally grounded.

Figure 26:
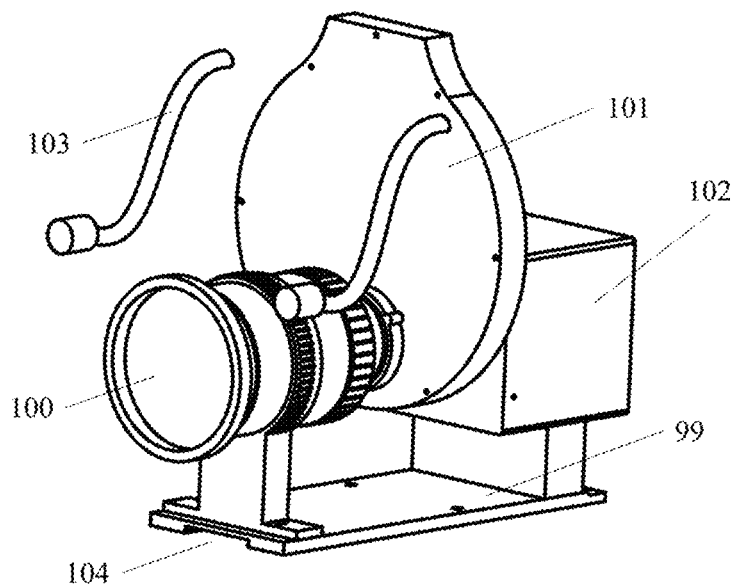
FIG. 26 shows a schematic diagram of a fluorescence detection module according to embodiments of the present disclosure.

FIG. 26 shows a schematic diagram of a fluorescence detection module according to embodiments of the present disclosure.

As shown in FIG. 26, the fluorescence detection module includes a sixth base 99, a third fixed focus lens 100, an emission light filter wheel 101, a fourth camera 102, an excitation light source, an excitation light filter wheel, and an excitation light fiber 103, which are connected together. The third fixed focus lens 100 may be a large aperture fixed focus lens. The fourth camera 102 may be a cooled camera. The dovetail groove 104 of the sixth base can be mounted on the guide rail on the adapter assembly 76, and can be quickly removed and replaced with other camera modules.

According to embodiments of the present disclosure, the fluorescence detection module is suitable for detecting fluorescent dyes and fluorescent proteins that require illumination of excitation light of a specific wavelength to generate a specific wavelength emission light signal, thus to study the distribution location and level of expression of the fluorescent dye and fluorescent protein in the plant sample body according to the emission light signal. A large aperture lens with an aperture F value less than 2.0 should be used, and a CCD or CMOS camera with cooling capability should be used.

According to embodiments of the present disclosure, a plurality of band-pass filters may be mounted on the emission light filter wheel 101 to allow only light in a specific wavelength range to pass. The computer controls the rotation of the filter wheel to move the specified filter to the front of the camera's photosensitive element.

According to embodiments of the present disclosure, LED cold light source or halogen lamp light source are used as the excitation light source. A plurality of band-pass filters are mounted on the excitation light filter wheel. The computer controls the rotation of the filter wheel to obtain excitation light of a specific wavelength. The excitation light can be conducted to the fluorescence detection module through the excitation light fiber 103, and irradiates the sample through a gooseneck on the module.

In order to improve the quality of image shooting, it is necessary to provide sufficient and moderate illumination for the sample. Therefore, there is an urgent need for a lighting device that can provide illumination of multiple angles and multiple areas.

According to embodiments of the present disclosure, the biological sample imaging equipment may further include a front imaging lighting module mounted on the three-dimensional displacement control device and located at an end of the three-dimensional displacement control device close to the incubator, for providing a front light source for the biological sample cultivation module through the observation window.

As shown in FIG. 1 and FIG. 22, the front imaging lighting module 79 can be mounted on the three-dimensional displacement control module outside the incubator 4, and located at the front end of the imaging module 3 carried by the three-dimensional displacement control module, and used to provide a front light source for imaging the sample placed inside the incubator 4 through the observation window of the sample closed incubator 4.

In embodiments of the present disclosure, in order to avoid blocking the imaging module 3 and affecting the imaging quality and illumination quality of the imaging module 3, the front imaging lighting module 79 may be mounted on a side of the imaging module 3 in order to avoid conflicts with the imaging range of the imaging module 3, that is, to prevent the front imaging lighting module 79 from appearing in the imaging range of the imaging module 3.

Further, in order to provide a uniform light source for the sample imaging, the front imaging lighting module 79 may be set as a ring light source, such as a ring LED light source with a diameter of 150 to 300 mm, wherein the center of the ring light source and the optical path of the imaging module 3 is concentric, and the area enclosed by the ring light source is larger than the area of the lens of the imaging module 3.

The ring light source can be on the same plane as the lens of the imaging module 3, or on a different plane from the lens of the imaging module 3. For example, as shown in FIG. 1, the plane on which the ring light source is located can be farther away from the sample than that of where the lens of the imaging module 3 is located, that is, the ring light source is non-contact sleeved on the imaging module 3. Of course, the plane where the ring light source is located can also be closer to the sample than that of where the imaging module 3 is located. The positional relationship between the ring light source and the imaging module 3 can be set and selected according to the needs of practical applications, which is not specifically limited in the present disclosure.

In embodiments of the present disclosure, the front imaging lighting module 79 may adopt an LED light source with a first wavelength, and the selection of the first wavelength may be determined according to the needs of practical applications, but the following conditions must be met: the sample is not sensitive to the first wavelength, but the imaging module 3 is sensitive to the first wavelength. For example, when the sample is a plant, the first wavelength can be set to 940 nm, which can provide infrared light illumination with a first wavelength to the plant to observe the growth state of the plant in the dark.

Figure 27:
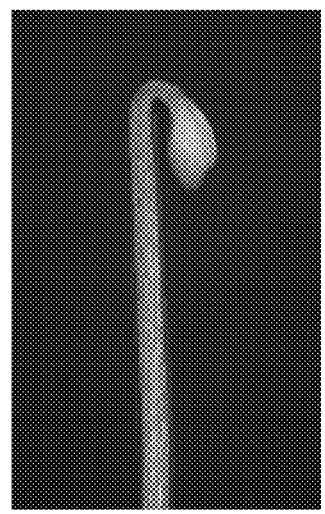
FIG. 27 shows an observation image of a plant sample obtained by using a front imaging lighting module according to embodiments of the present disclosure.

In embodiments of the present disclosure, the LED light source with the first wavelength may include a plurality of first sub-light sources, wherein the first sub-light sources may be lamp beads. The first sub-light sources face the center direction of the front imaging lighting module 79 and are uniformly or similarly arranged at a preset angle, wherein the preset angle can be set according to the needs of actual lighting applications, for example, it can be set to 30-60 degrees, the present disclosure does not specifically limit the specific value of the preset angle. Taking the preset angle being 30-60 degrees as an example, the front imaging lighting module 79 can achieve the effect of illuminating from 50-250 mm in front of the sample. For the plant sample grown in the incubator 4, this illumination method can produce the effect of a bright subject and dark background. Under the premise of high contrast of the subject and easy identification of the image subject, the texture of the subject is more detailed and clear, which is suitable for analyzing the hypocotyl growth rate, and tracking the local growth of the tissue. The observation image of the plant sample obtained by the above-mentioned irradiation method can be shown as an example in FIG. 27. According to embodiments of the present disclosure, the biological sample imaging device may further include a back imaging lighting module 81, mounted inside the incubator, and located at the back end of the sample, and used for providing a back light source for imaging the sample placed inside the incubator 4.

In embodiments of the present disclosure, a rotatable hollow polygonal sample table is placed inside the incubator 4 for placing samples to be observed. In this embodiment, the back imaging lighting module 81 is suspended on the top of the incubator 4 and located in the hollow part of the rotatable hollow polygonal sample table, and faces the sample and the observation window, so that the imaging module 3 mounted on the three-dimensional displacement control module can image the sample through the observation window after the back imaging lighting module 81 emitting a light source on the back of the sample.

In embodiments of the present disclosure, the back imaging lighting module 81 may be a surface light source. For example, the back imaging lighting module 81 may be a rectangular surface light source with a width of 130-200 mm and a height of 250-350 mm. The size of the surface light source can be set according to actual application requirements, and the present disclosure does not specifically limit it.

Figure 28:
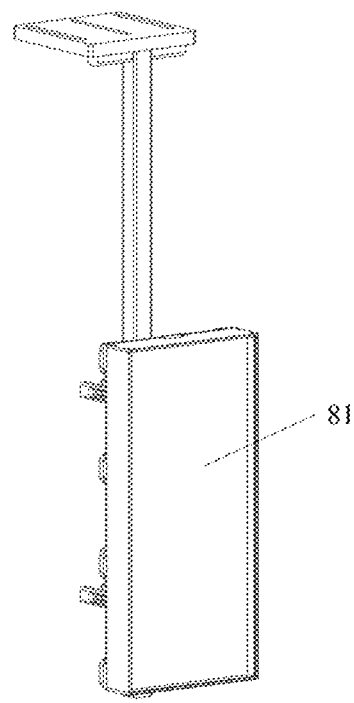
FIGS. 28-30 show schematic diagrams of a back imaging lighting module according to embodiments of the present disclosure.
Figure 29:
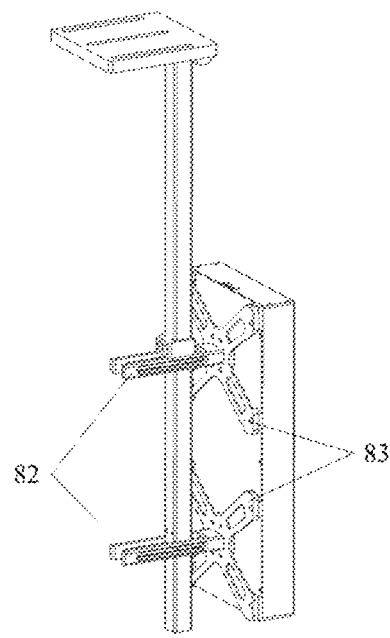
Figure 30:
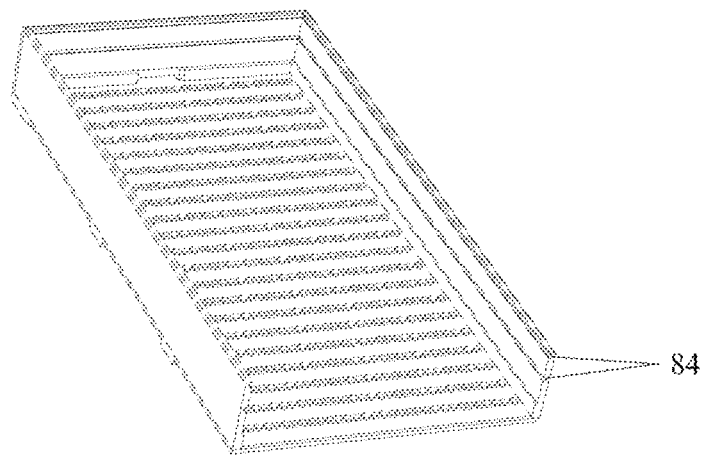

FIGS. 28-30 show schematic diagrams of a back imaging lighting module 81 according to embodiments of the present disclosure. As shown in FIG. 28 and FIG. 29, the back imaging lighting module 81 is suspended on the top of the incubator 4 by means of a connecting piece, so that the back imaging lighting module 81 can be hung in the hollow part of the rotatable hollow polygonal sample table.

The back imaging lighting module 81 is provided with a longitudinal fixing component 83 on the back, and a lateral fixing component 82 is mounted on the connecting piece. The back imaging lighting module 81 is fixed on the connecting piece by means of the connection between the longitudinal fixing piece 83 and the horizontal fixing piece 82. The longitudinal fixing component 83 is provided with connecting holes with different heights, and the connecting holes are used to connect the lateral fixing component 82 to the longitudinal fixing component 83 and provide connecting positions with different heights. In this way, the position of the back imaging lighting module 81 in the vertical direction can be adjusted by adjusting the connection position between the lateral fixing component 82 and the longitudinal fixing component 83, so that the back imaging lighting module 81 can face the sample and the imaging module 3, and enable the light source emitted by the back imaging lighting module 81 to cover the entire imaging range of the imaging module 3. The shape of the longitudinal fixing component 83 can be set according to the needs of the actual application, as long as the connection with the lateral fixing component 82 can be used to fix the back imaging lighting module 81 on the connecting piece.

The lateral fixing component 82 is provided with a slot hole on the side surface, and the position of the back imaging lighting module 81 in the horizontal direction can be adjusted by adjusting the fastening position of the screw in the slot hole.

In embodiments of the present disclosure, the back imaging lighting module 81 may adopt an LED light source with a second wavelength, which is similar to the first wavelength, and the selection of the second wavelength may be determined according to actual application requirements. However, the following conditions must be met: the sample is not sensitive to the second wavelength, but the imaging module 3 is sensitive to the second wavelength, wherein the second wavelength may be the same as the first wavelength or not the same. For example, when the sample is a plant, the second wavelength may be the same as the first wavelength, and both can be set to 940 nm.

As shown in FIG. 30, in embodiments of the present disclosure, the light source includes a plurality of second sub-light sources. Similarly to the first sub-light source, the second sub-light sources may also be a lamp bead. The second sub-light sources may be uniformly or substantially uniformly arranged on the surface of the back imaging lighting module 81, and the plurality of second sub-light sources may be divided into a plurality of sub-light source regions. The division of sub-light sources can be determined according to the actual lighting needs and the position of the sample and the imaging component. For example, each sub-light source area may include one row of second sub-light sources in the longitudinal direction, or two or more rows of second sub-light sources in the longitudinal direction. The light source area may also include some of the second sub-light sources in a row of second sub-light sources in the longitudinal direction. The sub-light source area may be irregularly shaped and composed of several second sub-light sources. Of course, the sub-light source area can also be divided horizontally, and the present disclosure does not specifically limit the specific division form of the sub-light source area. Taking each sub-light source area including a row of second sub-light sources in the longitudinal direction as an example, according to the total width of the second sub-light sources in the transverse direction, the back imaging lighting module 81 can be divided into 8-20 sub-light source areas.

According to this embodiment, the back imaging lighting module 81 can support a whole-area back-lighting mode and a partitioned back-lighting mode, and the lighting mode of the back imaging lighting module 81 can be selected or switched according to the needs of practical applications. For example, taking a plant sample as an example, the selection of the entire area back-lighting method or the partitioned back-lighting method can be determined according to the characteristics of the lighting method and the type of the plant sample. Specifically, the whole-area back-lighting method can eliminate the dark partial shadows caused by uneven surface of the culture medium or scratches of the sample, but the contrast of the main body contour will be reduced. The partitioned back-lighting method can improve the contrast of the main body contour, which is suitable for samples with weak contrast, and can simplify the mechanical structure to achieve the effect of simultaneously moving with the imaging range of the imaging module 3.

Taking each sub-light source area including a row of second sub-light sources in the longitudinal direction as an example, when the back imaging lighting module 81 adopts the whole-area back-lighting mode, all sub-light source areas are turned on. At this time, the back imaging lighting module 81 appears as a surface light source, illuminating the entire area evenly from the back of the sample. When the back imaging lighting module 81 adopts the partitioned back-lighting mode, a certain one or several sub-light source areas are individually turned on, and the back imaging lighting module 81 may appear as a longitudinal strip light source at this time. The TURN-ON position of the sub-light source area, that is, which one or several sub-light source areas are turned on, can be determined according to the position of the imaging module 3. Further, the horizontal position of the imaging module 3 can be determined according to the coordinate position in the horizontal direction provided by the three-dimensional displacement control module, thereby determining the TURN-ON position of the sub-light source area.

In embodiments of the present disclosure, a plurality of sub-light source areas share a common anode or a common cathode, and the other electrode is independently controlled by a control circuit to control the on and off of the plurality of sub-light source areas, thereby realizing the partitioned back-lighting of back imaging lighting module 81.

In embodiments of the present disclosure, the upper part of the light source surface of the back imaging lighting module 81, that is, the upper part of the plane where the second sub-light source is located, can also be provided with a layer or multiple-layer light homogenizing plates to evenly disperse the point light source emitted by the second sub-light source.

In embodiments of the present disclosure, a notch 84 is provided on the inner side of the back imaging lighting module 81 at a predetermined distance from the plane where the second sub-light source is located for mounting the light homogenizing plate. The number of the notches 84 may be one to mount the one or more layers of light homogenizing plates, or it may be consistent with the number of the light homogenizing plates, so that each notch 84 can be correspondingly mounted with one light homogenizing plate. The preset distance may be determined according to actual application requirements and the characteristics of the light source of the back imaging lighting module 81, which is not specifically limited in the present disclosure.

Figure 31:
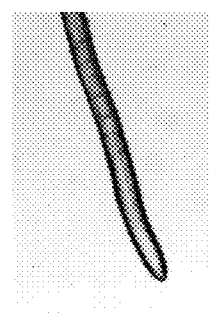
FIG. 31 shows an observation image of a plant sample obtained by using a back imaging lighting module according to embodiments of the present disclosure.

Compared with the front imaging lighting module 79, the back imaging lighting module 81 can produce an effect of a bright background and a dark subject, so that the outline of the sample outer edge is obvious. Still taking a plant sample as an example, the imaging based on the back imaging lighting module 81 is suitable for analyzing parameters such as root growth rate, leaf area and size, and the illustration image of the plant sample obtained by the above-mentioned illumination method can be shown as an example in FIG. 31.

According to the technical solution provided by embodiments of the present disclosure, the front imaging lighting module and the back imaging lighting module 81 that can respectively provide the front light source and the back light source, can be used alone or in combination according to actual application needs to achieve a variety of imaging effects such as bright subjects with dark backgrounds, or bright backgrounds with dark subjects. The above-mentioned technical solution can not only provide sufficient and moderate illumination for the sample, but also provide multi-angle and sub-regional illumination, so that the image shooting quality can be greatly improved. Taking the sample to be tested as a plant sample for example, the above technical solution can make the texture of the imaged subject more detailed and clear on the premise that the subject has a high contrast and is convenient for image recognition, which is suitable for analyzing the growth rate of hypocotyls by tracking the local growth of the tissue, and making the outer edge of the sample obvious, so as to be suitable for analyzing the root growth rate, leaf area size and other parameters. That is, it can provide a lighting device of multiple angles and multiple areas.

Above introduction has been made to the biological sample imaging device in embodiments of the present disclosure, and other representative usage modes will be listed as following. It should be noted that the biological sample imaging device provided in this embodiment has a variety of functions that can be arbitrarily combined, and the examples in this article are not an exhaustive list of all the combinations that users can use this device to achieve and the specific use of each module in the combination.

Example 1

Using a Large Horizontal Petri Dish Rack to Study the Germination and Seedling Growth of *Brassica Rapa* (Chinese Cabbage)

1. Sterilization of the petri dish: disassemble each part of the petri dish, wash with detergent and water, rinse with distilled water three times, and dry at room temperature; mount a sealing tape in the groove of the back cover and fix the front cover with screws, seal in a paper-sealed bag together with the top cover, after sterilization by ethylene oxide gas, disassemble the paper bag in the clean bench and take it out for use.
2. Surface sterilization of the *Brassica* seeds: put an appropriate amount of seeds in a 1.5 mL centrifuge tube, soak in 75% alcohol+0.01% Triton X-100 and fully shake for 15 minutes, pour out the liquid; rinse with 95% alcohol and pour the liquid; dry thoroughly in an open state in the clean bench, then close the tube cap tightly for later use.
3. Medium configuration: 4.33 g/L Murashige-Skoog salt mixture, 10 g/L sucrose, 3 g/L Phytagel plant gel, add deionized water to prepare 1 L culture medium, use KOH and HCl to adjust the pH to 5.7~5.8; sterilize at 121° C. for 15 minutes, cool to about 45~55° C., pour into the petri dish from the top opening, keep the liquid level about ½ to ⅔ of the total height; keep the petri dish stands vertically, and cover the top cover after the medium is solidified for use.
4. Seeding: put a piece of sterile filter paper in a sterile disposable ordinary petri dish in a clean bench, add a small amount of sterile water to soak the filter paper, and place the sterilized Brassica seeds on the filter paper. After swelling for 4 days in a dark environment at 4° C., take it out, use tweezers to carefully pick up the seeds showing white and place them on the surface of the culture medium, with an interval of about 10-20 mm, to make the white part of seeds face down; use a sealing film to seal the top opening without top cover; according to embodiments of the present disclosure, the top cover is not added during sowing and only the sealing film is used, which can ensure the internal sterile environment while promoting ventilation, and prevent the inner wall from condensing and condensed water flowing back to the surface of the culture medium when using this system for long-term cultivation and shooting, which causes the sample to be submerged by the condensed water and cause abnormal growth.

5. Mount the large horizontal petri dish rack: screw four M6*12 hexagon socket screws into the fixing holes on both sides of the rack, slide them into the mounting holes of the mounting fixture 35 on the rotating frame and tighten them, and insert the wiring of the overhead culture light source into the electrical socket interface 34.
6. Sample loading: place the front cover of the large petri dish with sample seeds facing outward in the groove of the rack, pull up 4 spring clips 56 and rotate them inward to fix the petri dish tightly.
7. Start each device module of the plant seedling imaging system: control the closed incubator 4 through computer software to provide a 22° C. constant temperature environment in the box; control the gas control module to continuously provide fresh air to the incubator; control the overhead light source 44 to provide mixing white light illumination; turn on the back infrared imaging lighting module, turn on all back-light partitions, and use 940 nm infrared light to provide illumination from the back of the sample; control the macroscopic phenotype detection module, the three-dimensional displacement system, and the eight-direction main bracket for continuous dynamic imaging, namely move the camera position and rotate the main bracket every set time interval (such as 5 min) to take a round of shooting for each petri dish.
8. Continue to perform continuous dynamic imaging to the predetermined time of the experiment; perform image data analysis.

Example 2

Embodiments of Microscopic Phenotyping to Study the Dynamic Details and Mechanism of *Arabidopsis* Seedlings' Shade Avoidance Response 1. Mounting imaging module: mount the microscopic phenotype detection module on the dovetail guide rail 76 of the three-dimensional displacement control module, and lock it through the positioning hole 77. The lens of the microscopic phenotype detection module uses a 4× magnified double telecentric lens.
2. Mounting plant cultivation module: mount 16 standard small vertical petri dish racks 36 on the mounting fixture 35 of the eight-direction main bracket; insert the wiring of the overhead cultivation light source 44 into the electrical socket interface 34. The overhead cultivation light source uses three-in-one LED lamp beads emitting three monochromatic lights of 660 nm red light, 735 nm far red light and 450 nm blue light at the same time.
3. Seed sterilization: the same as the seed sterilization method described above, and will not be repeated here.
4. Medium configuration: the same as the medium configuration method described above, and will not be repeated here.
5. Plant sample preparation: use tweezers to sow the sterilized seeds on the surface of the culture medium in a clean bench, and arrange them in a row with an interval of about 5 mm; seed one row in each petri dish, and the seeding height of a plurality of petri dishes should be the same; cover the petri dish lid and seal it with a sealing film; place it in environment of 4° C. away from light after swelling for 4 days, take it out and place it upright and cultivate it under 22° C. light for 5 days; grow the *Arabidopsis* seedlings upright against the surface of the medium; open the petri dish in the clean bench, select plants with good growth status and consistent phenotype, use tweezers to carefully hold up the cotyledon part, and transfer it to new medium, arrange plants in a row with an interval of 5 mm. Make sure each part of the plant is closely attached to the surface of the culture medium and avoid damage to the surface of the culture medium by the tweezers.
6. Sample loading: pull out the door pin 41 on the small petri dish module, open the first front cover 42, cover the petri dish without sealing film, put it vertically with the back facing outwards and the lid facing inward. Close the first front cover 42, reset the door pin 41, and tightly fix the petri dish in the small vertical petri dish rack 36 without moving.
7. Environmental variables control of plant cultivation: control the airtight incubator 4 through computer software to provide a 22° C. constant temperature environment in the incubator; control the gas control module to continuously provide fresh air in the incubator; control the overhead culture light source 44 to provide a mixed illumination of 660 nm red light, 735 nm far red light, and 450 nm blue light with a light intensity ratio of 3:1:3; close the incubator door and the operating window on the imaging darkroom, so that the environment of the plant sample is not interfered by external light.
8. Electronically controlled displacement device calibration: use the method described above to calibrate the zero point of the rotating platform 25 and the three-dimensional linear stage.
9. Record the initial position of the sample: turn on the back infrared imaging lighting module, turn on all the partitioned back-light channels, and use the surface light source mode; use computer software to control the angle of the rotating platform 25 so that the petri dish is facing the camera lens; control the horizontal displacement component 72 and the vertical displacement component 73 to make the lens aim at the photographed sample on the petri dish; control the depth displacement component 74 to make the lens focus clear, and record the coordinate data of the above 4 displacement stages for each sample to be photographed through the software.
10. Set the experimental condition plan: set parameters such as the time when the shade avoidance condition is applied and the total shooting time through the computer software.
11. Automatically control the start of dynamic imaging by software: automatically take a round of shooting every 5 minutes to obtain the image of each sample, that is, read the coordinate record of each sample, control the rotating platform and the three-dimensional linear stage to move to the specified position, and acquire and transfer the images for storage after the camera is exposed; in order to shorten the imaging time, the rotating platform should be controlled to move to the position of the next petri dish after all the samples in a petri dish are photographed. The samples in the same petri dish should be photographed in sequence in a serpentine way.
12. Treatment of shade avoidance conditions: 3 hours after the start of imaging, the computer software automatically controls the overhead culture light source 44 according to the preset plan, and changes the light intensity ratio of 660 nm red light, 735 nm far red light, and 450 nm blue light to 1:3:3.

13. Continue to perform continuous dynamic imaging for 10 hours; analyze the acquired image data and calculate the changes in the growth rate of the hypocotyls of *Arabidopsis* seedlings before and after the shade avoidance treatment.

Example 3

An Example of Microscopic Phenotyping, to Study the Rapid Response of *Arabidopsis* Seedlings to Ethylene Growth Inhibition 1. Mounting imaging module, seed sterilization and medium configuration are the same as that in Example 2;
2. Plant sample preparation: use tweezers to sow the sterilized seeds on the surface of the culture medium in a clean bench, and arrange them in a row with an interval of about 5 mm; seed multiple rows in each petri dish with an interval of about 20 mm; cover the petri dish lid and seal it with a sealing film; place it in environment of 4° C. away from light after swelling for 4 days, take it out and wrap it in aluminum foil and then place it upright at 22° C. and incubate in the dark for 2 days. Grow the *Arabidopsis* seedlings upright against the surface of the medium; use dim green LED bulbs for lighting in a completely dark room, open the petri dish in the clean bench, select plants with good growth status and consistent phenotype, use tweezers to carefully hold up it, and transfer it to new medium, and then arrange the plants in a row with an interval of 5 mm. Make sure each part of the plant is closely attached to the surface of the culture medium and avoid damage to the surface of the culture medium by the tweezers.
3. Sample loading: pull down the first fastener 61 on the airtight petri dish rack 38, open the second front cover 57 in the clean bench, and mount the petri dish without a cover into the inner box 59 vertically, close the second front cover 57; add 1000 μL of sterile distilled water to the water storage tank 65, and cover the T-shaped cover 66.
4. Mounting the plant cultivation module: mount the airtight petri dish rack 38 on the mounting fixture 35 of the rotating frame; insert the wiring of the overhead culture light source 44 into the electrical socket interface 34, or do not mount the overhead culture light source; use soft pipe to connect the gas inlet 63 on the airtight petri dish rack with the gas outlet on the electrical socket interface 34.
5. Environmental variables control of plant cultivation: control the airtight incubator 4 through computer software to provide a 22° C. constant temperature environment in the incubator; control the gas control module to continuously provide fresh air in the incubator; control the gas pump to ventilate each airtight culture module with a flow rate of 50 mL/min; turn off the overhead culture light source 44 to provide a dark growth environment; close the incubator door and the operating window on the imaging dark room, so that the environment of the plant sample is not interfered by external light.
6. Calibrate the electronically controlled displacement device and record the initial position of the sample as in Example 2.
7. Set the experimental condition plan: set parameters such as the time of ethylene condition application and withdrawal, target concentration, and total shooting time through computer software.
8. The software automatically controls the start of dynamic imaging as in Example 2.
9. Ethylene condition treatment: 2 hours after the start of imaging, the computer software automatically operates the gas control module according to the preset plan, and applies 10 ppm ethylene treatment to the closed incubator. For the specific method, refer to the description of the gas control system above.
10. Remove the ethylene treatment: 6 hours after the ethylene treatment is applied, the computer software automatically operates the gas control module according to the preset plan, uses high-pressure air to flush, and quickly exhausts the ethylene in the closed incubator. For the specific method, refer to the description of the gas control system above.
11. Continue to perform continuous dynamic imaging for 6 hours; analyze the acquired image data and calculate the rapid response of the growth rate of the hypocotyl and root of *Arabidopsis* seedlings to ethylene in the dark. The growth rate within 0.5 h after applying ethylene is significantly reduced. The growth rate returns to normal within 1 h after removal of ethylene.

Example 4

Example of Chemiluminescence Detection to Study the Effect of High Temperature on the Cycle Rhythm of *Arabidopsis* Seedlings 1. Mounting imaging module: Mount the luminescence detection module on the dovetail guide rail 76 of the three-dimensional displacement control module, and lock it through the positioning hole 77.
2. Seed sterilization: use transgenic *Arabidopsis* seeds expressing the CCA1::LUC gene, and the sterilization method is the same as that in Example 2.
3. Medium configuration: After sterilizing the medium at 121° C., add Luciferin fluorescein substrate solution filtered by a 0.22 μm sterile filter membrane when it is cooled to below 60° C. to a final concentration of 150 μg/ml. Shake the medium up and down gently; the others are the same as that in Example 2;
4. Plant sample preparation, sample loading, and plant cultivation module mounting are the same as that in Example 2;
5. Environmental variables control of plant cultivation: control the airtight incubator 4 through computer software to provide a 22° C. constant temperature environment in the incubator; control the gas control module to continuously provide fresh air in the incubator; turn on the overhead culture light source 44 to provide mixed white light illumination, and set an 18 h/6 h photoperiod with the light source turned off from 0:00 to 6:00 and turned on from 6:00 to 24:00 every day; close the incubator door and the operating window on the imaging dark room, so that the environment of the plant sample is not interfered by external light;
6. Calibration of the electronically controlled displacement device is the same as that in Example 2;
7. Record the initial position of the sample: turn on the front imaging lighting source to provide illumination for the sample; the method of controlling 4 displacement stages and recording coordinate data is the same as that in Example 2;

8. Determine the exposure time of the chemiluminescence signal: turn off the front imaging lighting source and the overhead culture light source, and expose for 2 minutes in a dark environment. Determine the exposure time for official shooting according to the brightness of the obtained image;
9. Set the experimental condition plan: set the time of applying high temperature conditions, target temperature, total shooting time and other parameters through computer software;
10. Automatically control the start of dynamic imaging by software: automatically take a round of shooting every 30 minutes to obtain the image of each sample, that is, read the coordinate record of each sample, control the rotating platform and the three-dimensional linear stage to move to the specified position; the camera performs exposure according to the time determined in step 8 to obtain the image and transfer it to the computer for storage; before the exposure starts, if the current time is in the photoperiod, turn off the overhead culture light source and let it stand in the dark for 30 seconds to avoid the interference of plant autofluorescence. Turn on the overhead culture light source again after the exposure is completed.
11. Treatment of high temperature conditions: 2 days after imaging starts, the computer software will automatically operate the airtight incubator according to the preset plan, and adjust the set temperature to 30° C. according to the preset plan.
12. Continue continuous dynamic imaging for 2 days; analyze the acquired image data and calculate the fluctuation period of CCA1::LUC expression and the change of phase affected by high temperature.

Example 5

Example of Fluorescence Detection to Study the Dynamic Changes of the Asymmetric Distribution of Auxin in the Roots of *Arabidopsis* Seedlings 1. Mounting the imaging module: Mount a colorless transparent filter (used for focusing and other bright field imaging) and a band-pass filter (used to detect the emission light of GFP green fluorescent protein) with a center wavelength of 530 nm and a half-peak bandwidth of 35 nm in the emission filter wheel; mount a band-pass filter with a center wavelength of 470 nm and a half-peak bandwidth of 30 nm in the excitation light filter wheel; mount the fluorescence detection module on the dovetail guide rail 76 of the three-dimensional linear displacement control module, and lock it through the positioning hole 77; adjust the excitation light fiber gooseneck to face the observation window of the incubator.
2. Seed sterilization: use transgenic *Arabidopsis* seeds expressing the DR5::GFP gene, and the sterilization method is the same as that in Example 2;
3. Method of medium configuration is the same as that in Example 2;
4. Plant sample preparation, sample loading and plant cultivation module mounting are the same as the sample preparation method described above;
5. Environmental variables control of plant cultivation: control the airtight incubator 4 through computer software to provide a 22° C. constant temperature environment in the incubator; control the gas control module to continuously provide fresh air in the incubator; turn on the overhead culture light source 44 to provide mixed white light illumination; close the incubator door and the operating window on the imaging dark room, so that the environment of the plant sample is not interfered by external light.
6. The calibration of the electronically controlled displacement device is the same as that in Example 2.
7. Record the initial position of the sample: turn on the front imaging lighting source to illuminate the sample, control the emission light filter wheel to switch to the transparent filter; the method of controlling 4 displacement stages and recording coordinate data is the same as that in Example 2.
8. Determine the exposure time of the fluorescent signal: turn off the front imaging lighting source and the overhead culture light source, control the excitation light filter wheel to switch to 470 nm band-pass filter, and control the emission light filter wheel to switch to 530 nm band-pass filter; turn on the fluorescent excitation light source, expose for 10 seconds, and determine the exposure time for the formal shooting according to the brightness of the obtained image; turn off the fluorescent excitation light source after each exposure.
9. Set the experimental condition plan: set the time of applying the gravity condition, rotation angle, total shooting time and other parameters through computer software;
10. Automatically control the start of dynamic imaging by software: control the excitation light filter wheel to switch to 470 nm band-pass filter, and control the emission light filter wheel to switch to 530 nm band-pass filter; automatically take a round of shooting every 10 minutes to obtain the image of each sample, that is, read the coordinate record of each sample, control the rotating platform and the three-dimensional linear stage to move to the specified position; the camera performs exposure according to the time determined in step 8 to obtain the image and transfer it to the computer for storage; automatically turn off the overhead culture light source at the beginning of each shooting cycle, and turn on it again after the imaging of all samples is completed; automatically turn on the fluorescent excitation light source before the exposure of each sample, and turn off it after the exposure.
11. Gravity condition processing: 2 hours after imaging starts, the computer software will automatically operate the servo motor of each gravity module according to the preset plan, read the respective current position readings, and calculate the position value after rotating 90° clockwise, and move to the corresponding position respectively; if a round of shooting of all sample has not been completed at the time scheduled for the experiment, wait for the completion of the round of sample shooting before operating the servo motor.
12. Continue to perform continuous dynamic imaging for 1 day; analyze the distribution of auxin represented by DR5::GFP in the plant body and the changes in the expression of each part with the growth of the roots with heavy bending according to the acquired image data.

The technical solutions provided by the various embodiments of the present disclosure have at least the following beneficial effects:
1. High-throughput imaging of plant seedlings: the previous design can either shoot seedlings (can take macro images and distinguish micron-level length changes) but cannot take a large number of samples (high throughput) at the same time, or can take high-throughput but only large plants without sufficient physics resolution to analyze the seedlings. This invention can help scientific researchers who take plant seedlings as research objects to greatly improve the accuracy of quantitative analysis of plant dynamic growth. In addition, since the statistical analysis requires multiple biological replicas of experimental data for the same sample, and the traditional experimental methods can only shoot one or a small number of samples each time, therefore, it will take several weeks or even months to obtain sufficient statistical data, which is an impossible task in practice. This invention can shorten the labor and time expenditure of scientific researchers, and quickly obtain statistically significant data that can be used for high-quality academic research topics.

2. Combination of multiple experimental conditions: in scientific research, it is always necessary to change the experimental condition variables for experimental result changes observation to explore the internal mechanism of the influence of each variable. This invention can automatically control the temperature, gas component concentration, light, gravity and other conditions in the cultivation environment of the plant seedling sample while taking high-throughput imaging analysis. It can periodically and quantitatively change the most common environmental variables in the growth and development process of the above plants, and can also combine the control of multiple environmental variables, and analyze the microscopic dynamic growth changes on this basis. These are impossible for existing experimental methods. For example, researchers who study the plant hormone ethylene can use the present invention to study the rapid changes in the growth rate of plants before and after treatment with ethylene. Researchers who study the gravity induction of roots can study the instantaneous effects of changes in the direction of gravity and light on growth. Researchers who study the resistance of plants to adversity can study the dynamic changes of plant growth rates under conditions such as high temperature or hypoxia.

3. Expandable multifunctional module: Petri dish racks that can be mounted on the rotating frame include small vertical petri dishes, large horizontal petri dishes, airtight petri dishes, gravity petri dish rack, etc. It can be mounted separately or in combination to realize the adaptation to different types of samples and different experimental purposes. The imaging detection module that can be mounted on the camera adapter assembly includes a variety of modules such as the microscopic phenotype module, the macroscopic phenotype module, the high-sensitivity luminescence module, the fluorescence module, etc., which can observe different types of phenotypes and realize the integration of multiple experimental methods. At the same time, the adapter brackets all adopt a universal interface design, and can connect to more functional modules to provide expansion for future new functions.

The above description only explains preferred embodiments of the present disclosure and the applied technical principles. Those skilled in the art should understand that the scope of the invention involved in the present disclosure is not limited to the technical solutions formed by the specific combination of the above technical features, and it should also cover other technical solutions formed by any combination of the above technical features or their equivalent features without departing from the inventive concept. For example, the above-mentioned features and the technical features disclosed in the present disclosure (but not limited to) having similar functions can be replaced with each other to form a technical solution.

The invention claimed is:

1. A biological sample imaging device, comprising:
an incubator with an observation window provided on one side;
a biological sample cultivation module provided inside the incubator;
an imaging module provided outside the incubator and arranged on a three-dimensional displacement control device through an adapter assembly, for collecting images of a biological sample cultured in the biological sample cultivation module through the observation window,
wherein the biological sample cultivation module comprises:
a rotating frame comprising a rotating platform and a frame body, wherein the frame body is fixed to the rotating platform, and a plurality of mounting positions for petri dish racks are arranged on the frame body; and
one or more petri dish racks detachably mounted on the mounting positions and configured for fixing one or more petri dishes,
wherein the frame body comprises first brackets and second brackets, wherein the first brackets are distributed radially, each second bracket is fixed to an end of a first bracket extending out of the rotating platform in an axial direction, and a mounting position is formed in a space between two adjacent second brackets,
wherein at least two mounting fixtures are fixed on two adjacent second brackets arranged at different heights, and the mounting position is formed between mounting fixtures of the two adjacent second brackets
wherein the plurality of mounting positions are arranged radially around the rotating frame and stacked axially along an axis of rotation of the rotating frame at different heights whereby a petri dish is positioned adjacent the observation window by rotating the rotating frame and the imaging module is moved in three-dimensions such that the petri dish is in view of the imaging module.

2. The device according to claim 1, further comprising an optical vibration isolation platform, wherein an opening is provided on bottom of the incubator, and the biological sample cultivation module is fixed to the optical vibration isolation platform through the opening.

3. The device according to claim 1, further comprising a housing, which is provided outside the incubator and the imaging module and forms a dark room for shielding light.

4. The device according to claim 1, further comprising a computer for controlling operation of the incubator, the biological sample cultivation module and the imaging module, and receiving biological sample images.

5. The device according to claim 1, wherein:
a heating element is mounted around the observation window; and/or
both sides of the observation window are covered with coatings to increase light transmittance of the observation window in visible light and/or infrared light waveband.

6. The device according to claim 1, wherein:

the incubator comprises a box, a temperature control system and a gas control system;

the temperature control system includes at least one temperature sensor, a control circuit, a compressor, a condenser, an evaporator, and a circulating fan, wherein the compressor is arranged outside the box; and the gas control system includes a gas source, a gas mixing device and a gas sensor.

7. The device according to claim 6, wherein the gas mixing device comprises:

a plurality of gas paths corresponding to the gas source;

a controller configured to control gas flow of the plurality of gas paths by controlling stop valves and flow controllers of the plurality of gas paths; and a gas mixing tank, which is connected to the plurality of gas paths and a gas inlet of the incubator and configured for mixing gas, wherein, the gas source includes one or more of a nitrogen gas source, an ethylene gas source, a carbon dioxide gas source and an air source.

8. The device according to claim 1, wherein:

the mounting fixtures are fixed at different heights of the same second bracket.

9. The device according to claim 1, wherein:

the mounting fixtures comprises at least two mounting holes for mounting a small petri dish rack on one side of each mounting fixture; and/or the mounting fixtures comprises at least four mounting holes for mounting two or more small petri dish racks or at least one large petri dish rack on one side of each mounting fixture, wherein the small petri dish rack comprises any one of a small vertical petri dish rack, an airtight petri dish rack, and a gravity petri dish rack, and the large petri dish rack includes a large horizontal petri dish rack.

10. The device according to claim 1, wherein the rotating frame further comprises:

a distributor plate fixed above the rotating platform;

a conductive slip ring arranged inside the rotating platform;

a plurality of electrical socket interfaces provided on the second brackets;

a plurality of cables connected with the conductive slip ring and connected to the electrical socket interfaces via the distributor plate.

11. The device according to claim 10, wherein:

a top of the rotating platform is provided with a plurality of mounting holes for fixing the first brackets and the distributor plate; and the first brackets are fixed between the distributor plate and the rotating platform.

12. The device according to claim 1, wherein the rotating platform comprises:

a base, a flange fixed to the base;

a baffle fixed to the flange and provided with a notch;

a photoelectric limit switch fixed on the base and having a height adapted to the baffle.

13. The device according to claim 1, wherein the rotating frame further comprises:

a gas pump fixing plate;

a plurality of gas pump damping sleeves fixed to the gas pump fixing plate; and a gas pump arranged inside the gas pump damping sleeves, wherein the second brackets are provided with a pneumatic connector, which is connected to the gas pump through a gas pipeline.

14. The device according to claim 1, wherein:

the rotating frame further comprises a liquid pump, which is arranged on the rotating platform;

a liquid delivery connector is provided on at least one second bracket; and the liquid pump is connected to the liquid delivery connector through a liquid pipeline.

15. The device according to claim 1, wherein the frame body further comprises a corner reinforcement block, which is arranged at a connection between a first bracket and a second bracket.

16. The device according to claim 1, wherein at least one of the petri dish racks comprises:

a first lighting component arranged inside a frame of the at least one petri dish rack; and/or a second lighting component arranged on a top of the at least one petri dish rack.

17. The device according to claim 1, wherein:

the adapter assembly has a horizontal platform surface which is provided with a guide rail and a positioning pin hole;

the guide rail is configured to provide a sliding path of the imaging module;

the positioning pin hole is configured to position the imaging module, wherein the imaging module comprises any one of a microscopic phenotype detection module, a macroscopic phenotype detection module, a luminescence detection module, and a fluorescence detection module.

18. The device according to claim 17, further comprising:

a front imaging lighting module mounted on an end of the three-dimensional displacement control device close to the incubator and configured to provide a front light source for the biological sample cultivation module through the observation window; and/or a back imaging lighting module mounted inside the incubator and configured to provide a back light source for the biological sample cultivation module.

19. The device according to claim 1, wherein:

some of the mounting fixtures are fixed at a same height of a plurality of second brackets.

* * * * *